(12) United States Patent
Tarabishy

(10) Patent No.: US 6,755,865 B2
(45) Date of Patent: Jun. 29, 2004

(54) JOINT PROSTHESIS AND METHOD FOR PLACEMENT

(76) Inventor: Imad Ed. Tarabishy, 4275 River Birch Dr., Spring Hill, FL (US) 34607

( * ) Notice: Subject to any disclaimer, the term of this patent is extended or adjusted under 35 U.S.C. 154(b) by 0 days.

(21) Appl. No.: 09/961,662

(22) Filed: Sep. 24, 2001

(65) Prior Publication Data

US 2003/0060889 A1 Mar. 27, 2003

(51) Int. Cl.⁷ .................................................. A61F 2/32
(52) U.S. Cl. ............................... 623/22.12; 623/22.42; 606/80; 606/81
(58) Field of Search ........................... 623/19.12, 22.11, 623/22.12, 22.15, 22.17, 22.18, 22.19, 22.21, 22.24, 22.27, 22.28, 22.42, 23.43; 606/91, 80, 81; A61F 2/32, 2/34

(56) References Cited

U.S. PATENT DOCUMENTS

| | | | |
|---|---|---|---|
| 4,662,891 A | * | 5/1987 | Noiles .......................... 623/22 |
| 5,007,935 A | | 4/1991 | Vincent et al. |
| 5,133,764 A | | 7/1992 | Pappas et al. |
| 5,425,778 A | | 6/1995 | Zichner et al. |
| 5,725,597 A | * | 3/1998 | Hwang .......................... 623/23 |
| 5,735,901 A | * | 4/1998 | Maumy et al. ............... 623/18 |
| 5,807,407 A | | 9/1998 | England et al. |
| 5,989,294 A | | 11/1999 | Marlow |
| 6,010,535 A | | 1/2000 | Shah |
| 6,110,211 A | * | 8/2000 | Weiss ....................... 623/23.11 |
| 6,283,971 B1 | * | 9/2001 | Temeles ....................... 606/81 |
| 6,361,566 B1 | * | 3/2002 | Al-Hafez .................. 623/22.15 |
| 6,589,281 B2 | * | 7/2003 | Hyde, Jr. .................. 623/18.11 |

* cited by examiner

Primary Examiner—David H. Willse
Assistant Examiner—Javier G. Blanco
(74) Attorney, Agent, or Firm—Pettis & Van Royen, P.A.

(57) ABSTRACT

A prosthesis for replacement of a ball and socket joint in the human body. The prosthetic components comprise a plurality of separate parts which may be inserted through a hole in the femur of the patient and assembled and attached to the prepared acetabulum of the hip bone to form a cup-shaped first shell. A cup is also passed through the hole in the femur and attached to the first shell to form the socket portion of the joint. A shaft having a first end with a ball formed thereon is inserted in the hole through the femur so that the ball engages the cup for movement therein.

8 Claims, 21 Drawing Sheets

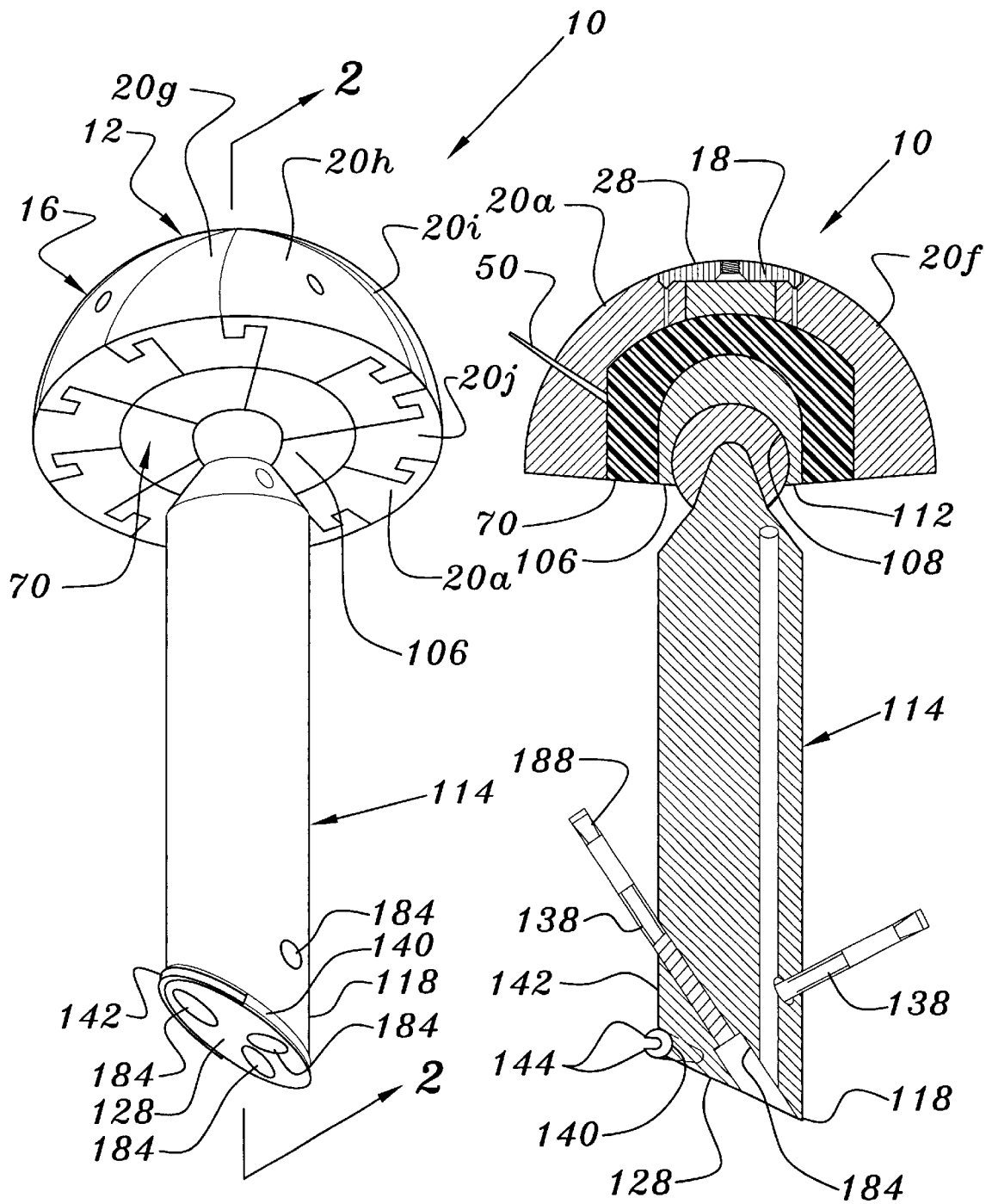

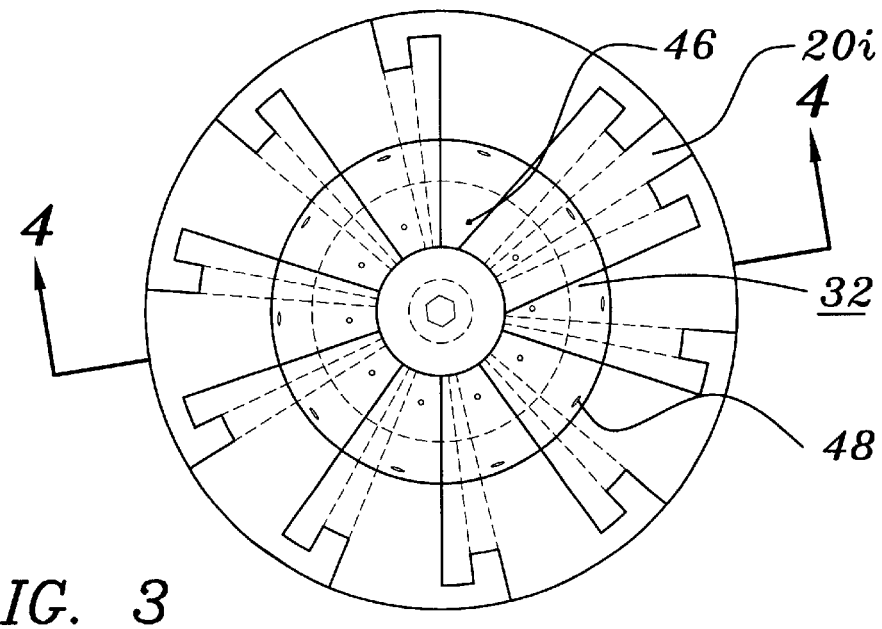
FIG. 3
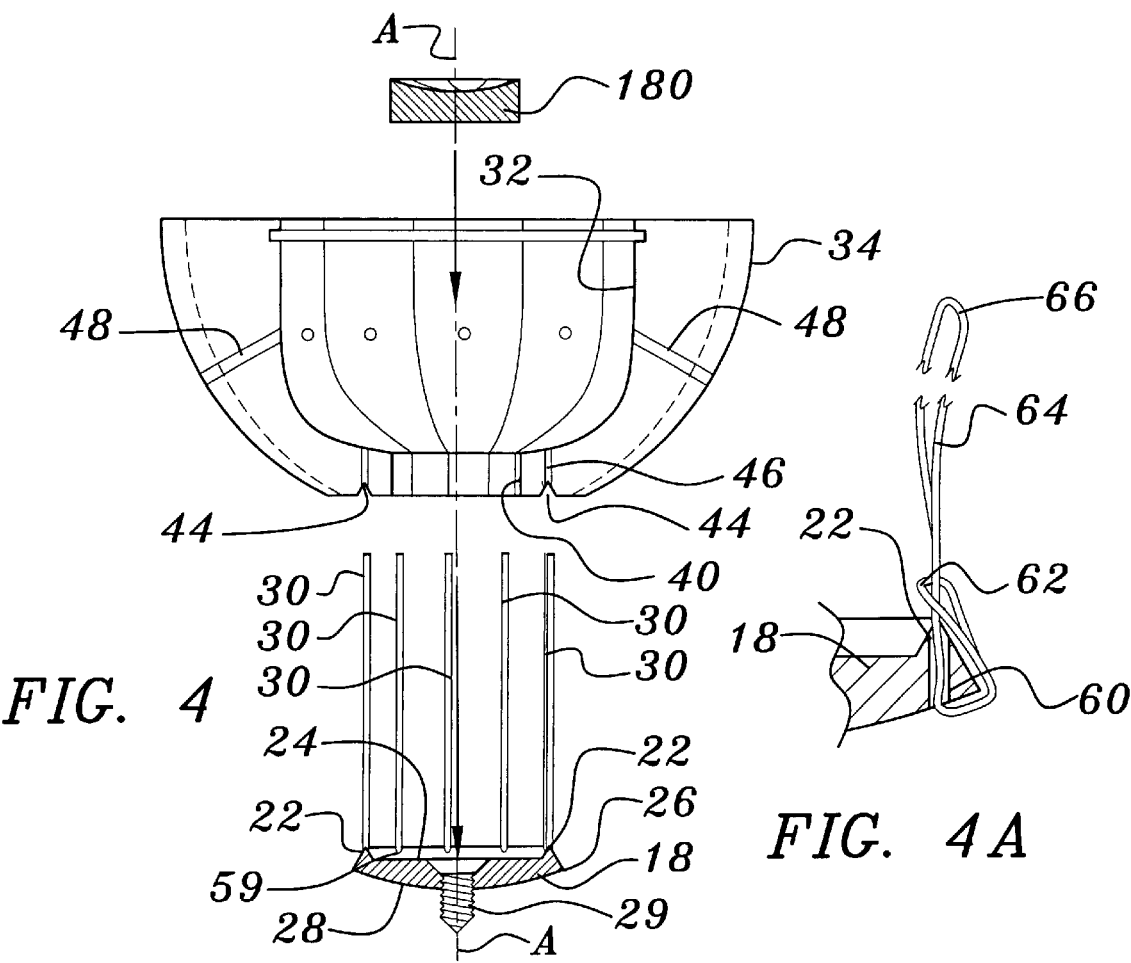
FIG. 4
FIG. 4A

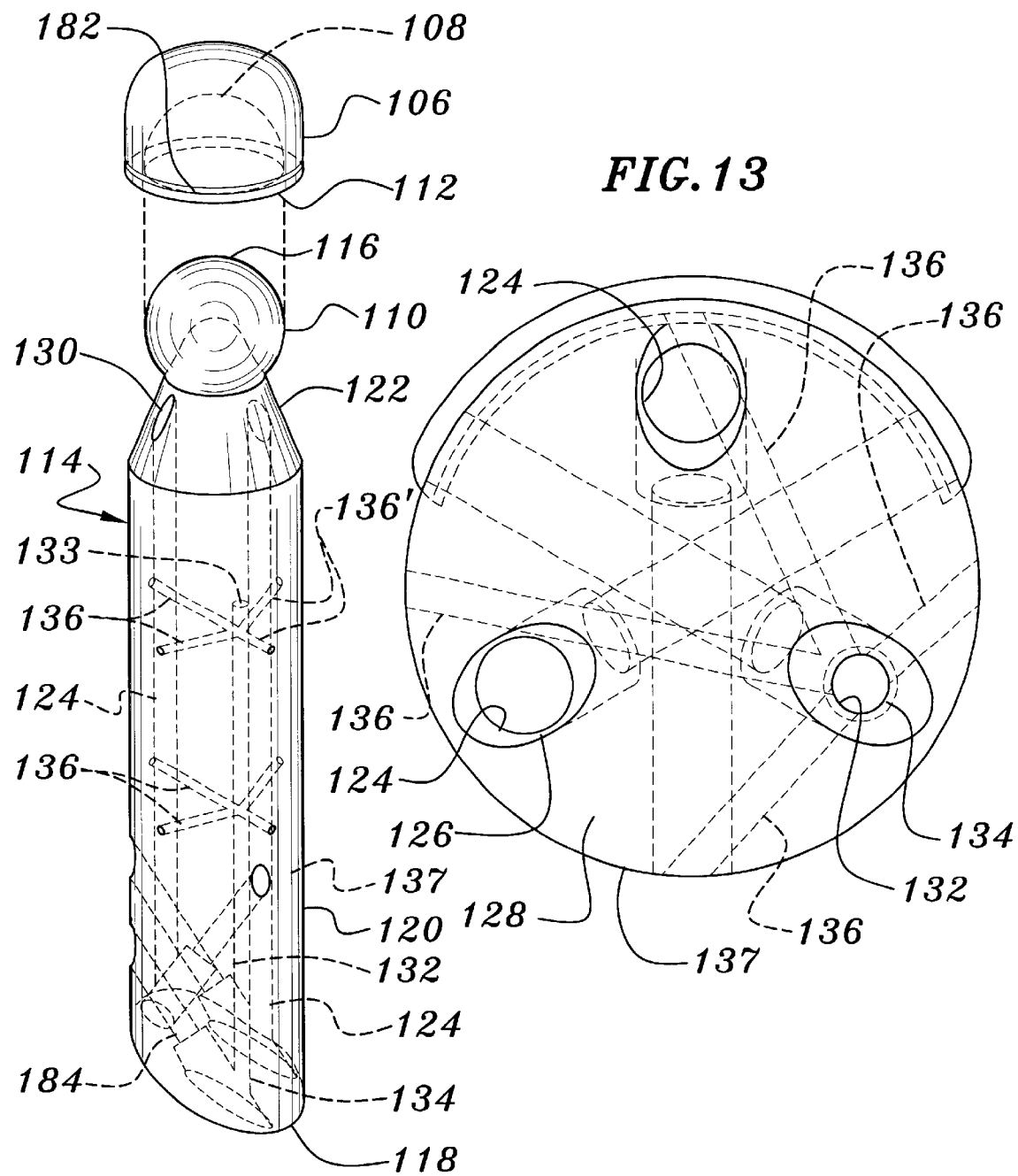

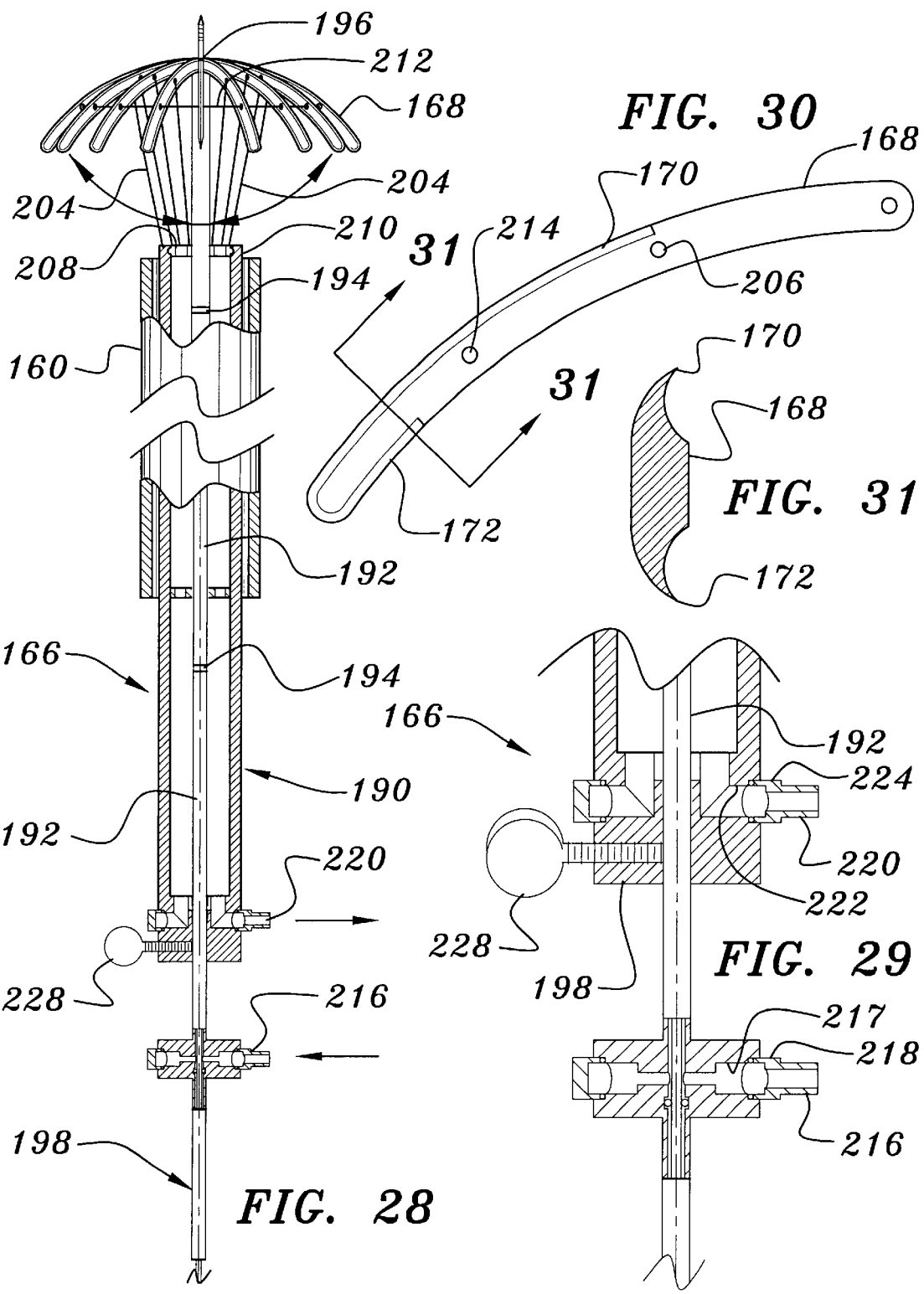

JOINT PROSTHESIS AND METHOD FOR PLACEMENT

BACKGROUND OF THE INVENTION

1. Field of the Invention

The present invention relates to a device for total joint replacement, and more particularly to hip and shoulder joint prostheses that require less invasive surgery during installation than required by the current prostheses and methods for placement.

2. Description of the Prior Art

Arthroplasty, the restoration of normal joint motion, is frequently done by the insertion of metallic prostheses. Implant technology has improved over the last number of years and provides solutions to problems caused by injury, arthritis and other joint diseases. Frequently, the damage is sufficiently severe to require a total joint replacement. The prior art discloses numerous designs for total hip joint prosthetic devices.

Total hip joint replacements require interactive prosthetic femoral and acetabular components to emulate the ball-socket mechanism of a natural hip joint. When the supporting structure is weakened, particularly the femoral head and neck, a prosthetic femoral component with an extended shaft is implanted within the medullary cavity of the femur. Examples of this type total hip replacement prosthetic device are disclosed in U.S. Pat. No. 6,093,208 issued to Enrico Tian and U.S. Pat. No. 5,807,407 issued to England, et al. Many surgeons take this route, even when the underlying bone structure of the femoral head and neck is strong, under the theory that implantation of the shaft within the medullary cavity of the femur is required to obtain the necessary support for the prosthetic femoral head, as the femoral implant is under high stresses that can cause failure of "surface replacement" devices. Such failures frequently occur early in the patient's recovery, before the bonding of the bone to the metal surfaces of the prosthetic implant has occurred. However, the insertion of the prosthetic device with a long femoral shaft requires the resection of the femoral head and neck to obtain access to the longitudinal cavity within the femur. Such surgery is very stressful to the patient and increases the risk of infection. If the device fails, any further implantation of prosthetic devices becomes exceedingly difficult, as the supporting bone structure has already been appreciably reduced.

U.S. Pat. No. 5,800,558 to Gerald A. LaHaise, Sr., U.S. Pat. No. 5,133,764 to Pappas et al., and U.S. Pat. No. 4,846,841 to Indong Oh, disclose the "surface replacement" technique of a total replacement of a hip joint. "Surface replacement" is aimed at primarily providing replacement of the joint surfaces while preserving as much of the supporting bone structure as possible and preserving the integrity of the medullary cavity. Pappas et al. '764 and Oh '841 each disclose a version of a cap that is implanted over the resected head of the femur. LaHaise '558 discloses a more complex means for attaching the ball to the resected head of a femur. One advantage to the surface replacement type of total hip replacement, is that much of the femur is left intact, so that if the surface replacement method fails, it may be replaced with an intramedullary canal prosthetic component.

Each of the above patents disclose a generally solid metal acetabular cup that is fixed, usually by screws, to a prepared surface of the hip bone. An insert, a layer of plastic or metal is frequently attached to the acetabular cup, the insert being sized to receive the ball portion of the prosthetic joint that is attached to the femur.

Each of these prostheses mentioned above, are installed during lengthy, invasive, major surgery that requires surgically opening the hip area for full exposure and direct access to the hip joint. During surgery the head of the femur must be removed from the acetabular cup, for resection of the femur head or complete removal of the femur head and neck. This surgery comes at a high cost as it is complex, requiring extensive surgical support staff and operating room equipment.

Not withstanding the existence of such prior art prosthetic components and methods for attachment to the human body, it remains clear that there is a need for prosthetic components that may be inserted into the human body without a major incision gain direct access to the femur and hip bone.

SUMMARY OF THE INVENTION

The present invention relates to a prosthesis and method for implantation of that prosthesis within the human body as the replacement for a ball joint. The apparatus comprises at least one segmented shell that is attachable to the acetabulum of the hip bone of a patient. The segmented shell comprises a plurality of separate parts which may be inserted through a hole in the femur of the patient and assembled and attached to the hip bone to form a cup-shaped first shell.

A cup whose exterior is sized and configured to be received tightly within the interior of the first shell is also passed through the hole in the femur and then attached to the first shell. The interior of the cup is sized and configured to receive the ball portion of the prosthetic component.

A shaft having a first end with a ball formed thereon, that is sized and configured to be received within the cup is inserted within the hole through the femur so that the ball engages the cup for movement therein.

As the head of the femur and the acetabulum is larger than any hole that can be made through the neck of the femur, an expandable drill bit must be used to remove the head of the femur and a thin portion of the outer layer of the acetabulum.

The invention accordingly comprises an article of manufacturer possessing the features, properties, and the relation of elements which will be exemplified in the article hereinafter described, as well as the method for insertion of the article into the human body. The scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which:

FIG. 1 is an isometric view of the hip joint prosthesis of this invention;

FIG. 2 is a cross-sectional elevational view taken along line 2—2 of FIG. 1;

FIG. 3 is a top plan view of the segmented first shell of the prosthesis of FIG. 1;

FIG. 4 is an exploded cross-sectional view of FIG. 3 taken along line 4—4;

FIG. 4A is a detailed view illustrating the use of surgical thread in the place of wires 30;

FIG. 13 is a bottom plan view of the shaft of FIG. 12;

FIG. 28 is a front elevational view of the expendable drill bit used to remove the head of the femur, illustrating the blades extended outwardly;

FIG. 29 is a detailed view of the first end of the expandable drill bit of FIG. 28;

FIG. 30 is a detailed view of one of the blades of the cutter of FIG. 28;

FIG. 31 is a cross-sectional view taken along line 31—31 of FIG. 30;

Similar reference characters refer to similar parts throughout the several views of the drawings.

DESCRIPTION OF A PREFERRED EMBODIMENT

Figure 5:
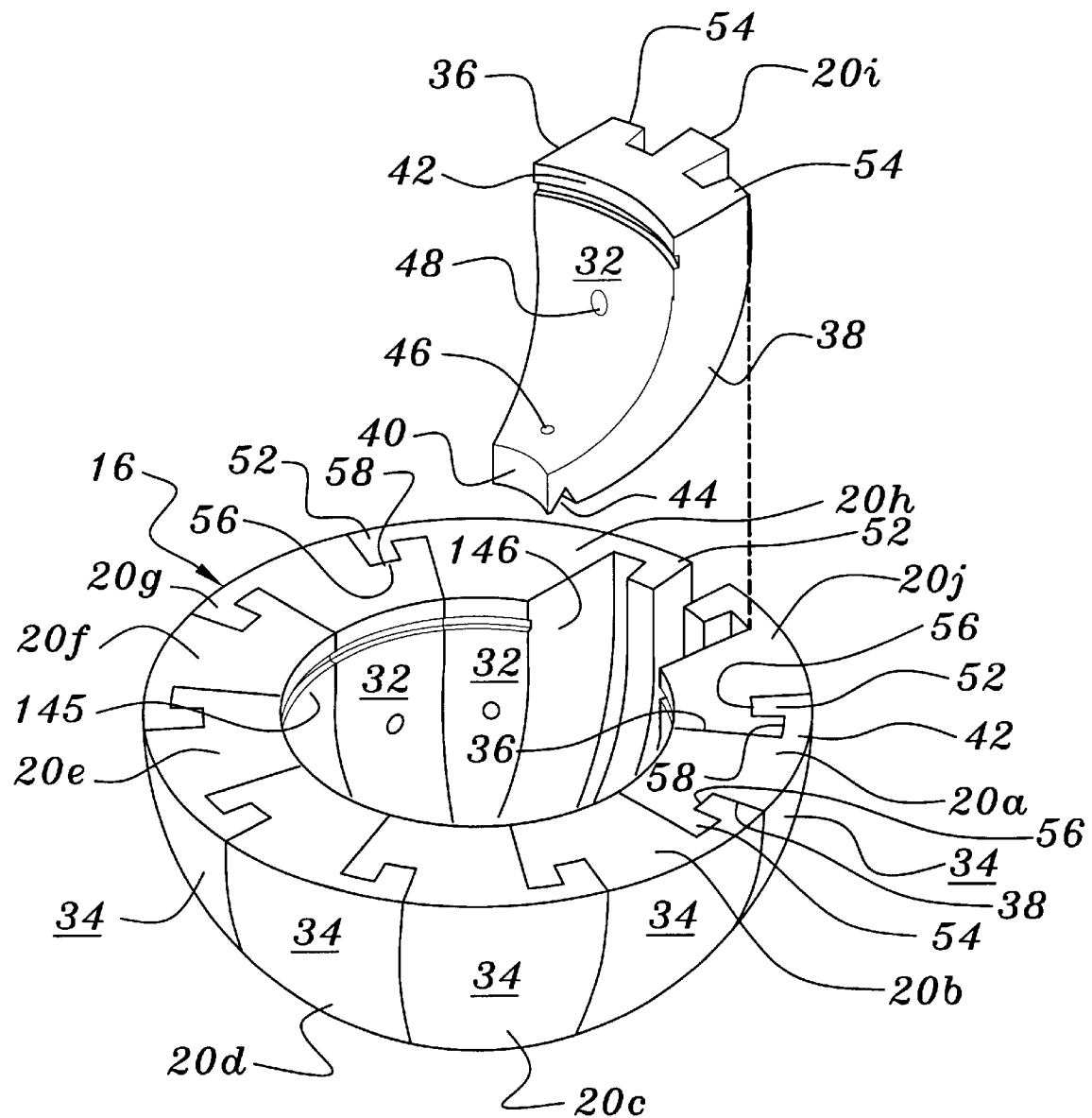
FIG. 5 is an isometric view of the segmented first shell of FIG. 3 with the key segment exploded.

A preferred embodiment for the prosthetic components of this invention are illustrated in the drawing FIGS. 1–13, in which the apparatus is generally indicated as 10. The prosthetic implants for replacement of a natural ball and socket joint and the method of placement of such components, as disclosed in this application, particularly illustrate a total hip joint replacement; however based upon the teachings of this patent, those skilled in the art will be able to modify these prosthetic implants to serve as a total shoulder joint replacement. Those skilled in the art will also be able to modify the steps for placement of a hip prosthesis, as taught by this patent, to implant a shoulder prosthesis. Referring first to the view of FIG. 1, it can be seen that the prosthetic components of this invention comprise a socket implant, shown generally as 12, and a ball implant, conveniently shaft 114. The ball implant is received by the socket implant to complete the mechanical joint for replacement of the natural joint.

For a total hip joint replacement, the acetabulum of the patient is prepared for receipt of the socket implant 12 and the femur is prepared for receipt of the ball implant. For a total shoulder joint replacement, the glenoid cavity of the scapula is prepared for receipt of a socket implant and the humorous bone is prepared for receipt of the ball implant. In the case of a shoulder joint, the portion of the socket implant that is attached directly to bone may be solid or segmented, as the shoulder socket implant is much smaller than the hip socket implant, and the size of the humorous bone in comparison with the femur supports a larger access bore for passing a solid shoulder socket implants therethrough. In both cases, the natural ball and socket joint is replaced with a mechanical one.

For purposes of illustration, the hip joint will be used to illustrate the apparatus and method of implantation. A preferred embodiment of the socket implant 12 is illustrated in the FIGS. 1–13, and comprises a first segmented shell 16 made of metal, a second segmented shell 70 made from synthetic resin, and a metal cup 106. In other preferred embodiments, structure of the socket implant 12 of the prosthetic components 10 will be modified according to the need, to form two additional embodiments, 310 and 610.

Figures 14, 15:
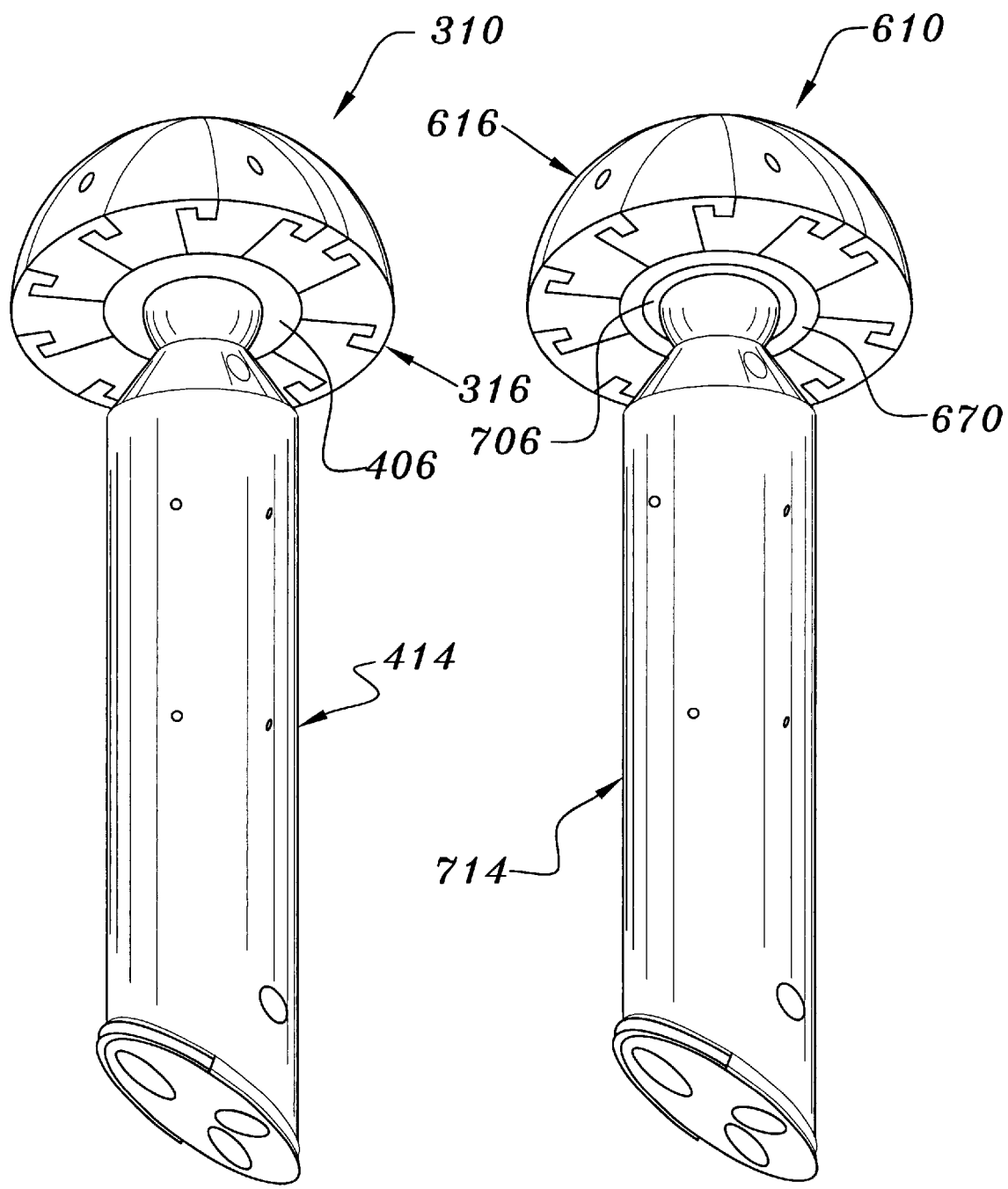
FIG. 14 is an isometric view illustrating a second preferred embodiment of the hip joint prosthesis of this invention.
FIG. 15 is an isometric view illustrating a third preferred embodiment of the hip joint prosthesis of this invention.
Figure 22:
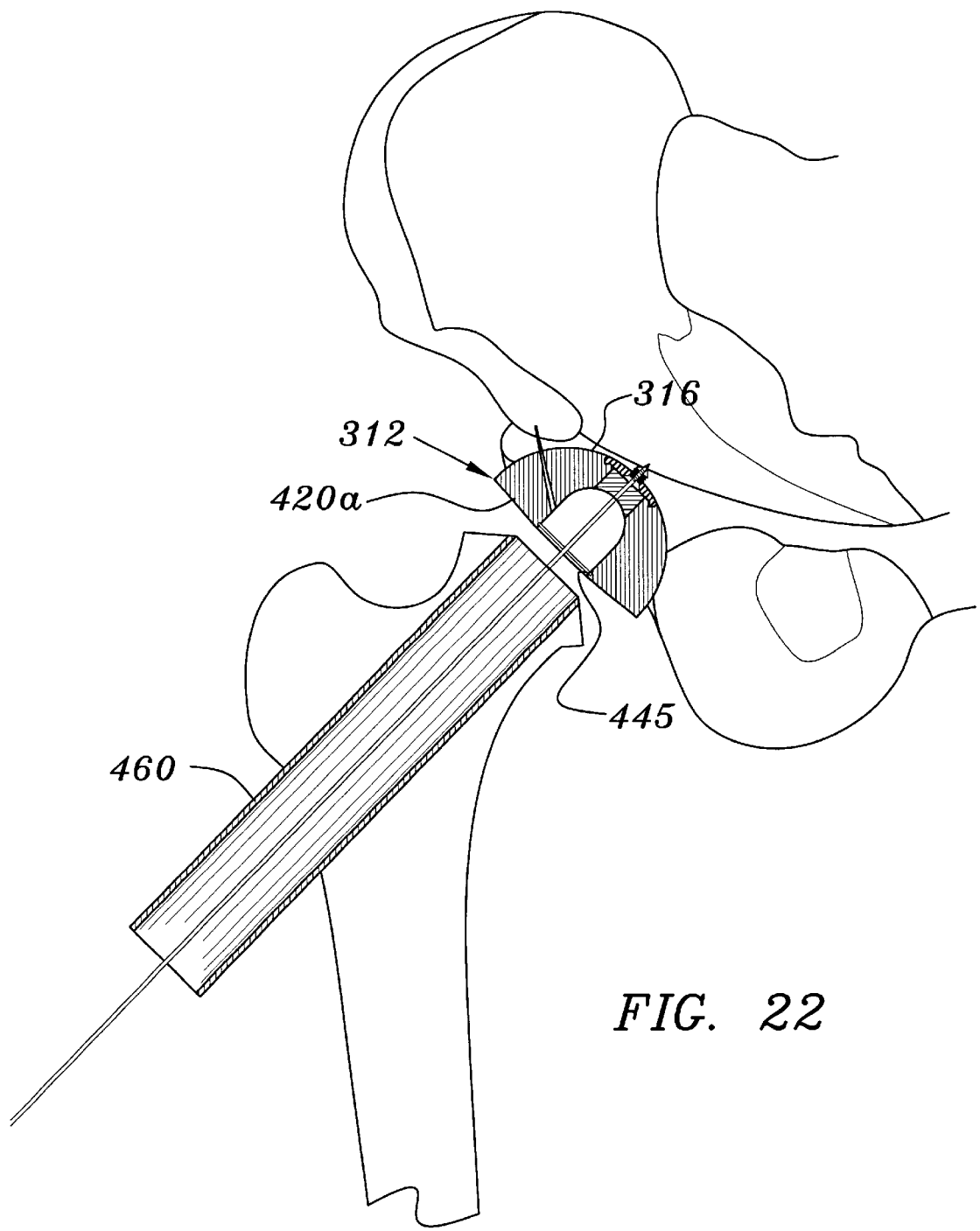
FIG. 22 illustrates the placement of a segmented first shell of this invention having thick segments.
Figures 12, 23:
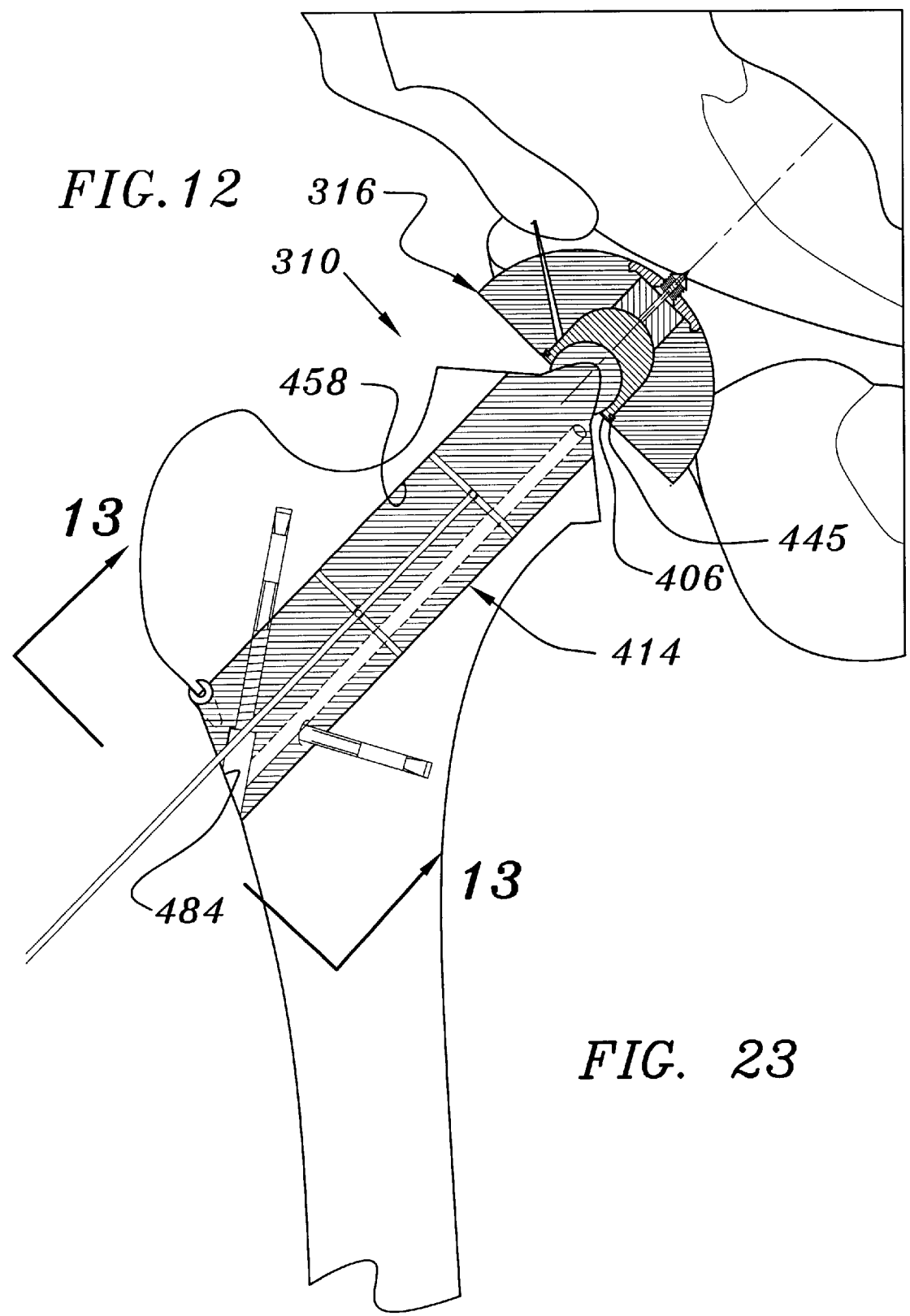
FIG. 12 is an isometric view of the shaft and cup of this invention.
FIG. 23 illustrates the placement of the cup within the segmented first shell of FIG. 22 and placement of the shaft into the hole bored through the femur so that the ball engages the cup.

In a second preferred embodiment of the prosthetic components, indicated as 310, and as illustrated in FIGS. 14, 22, and 23, the socket implant 312 is comprised of a segmented metal first shell 316 and a cup 406 that is received by the first shell, the cup being made from metal or plastic. In order to use a single segmented shell and a cup, the patient receiving the prosthetic components 310 must have large bones so that the hole bored through the neck of the femur is large enough to allow thicker segments to pass therethrough and/or a greater number of thicker segments.

Figure 27:
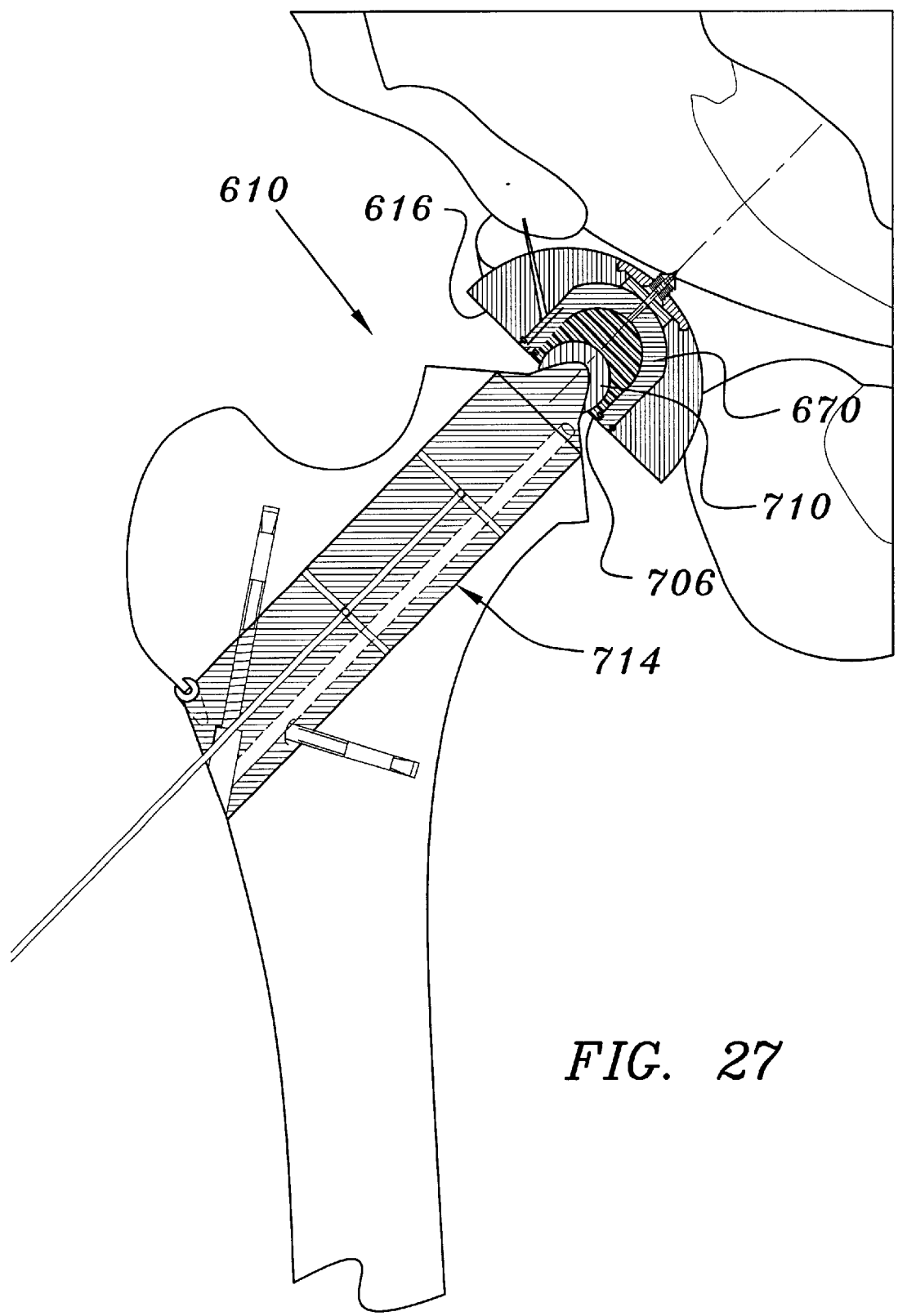
FIG. 27 illustrates the placement of the segmented first shell, a solid second shell, a cup and the shaft that is inserted into the hole bored through the femur so that the ball engages the cup.

In third preferred embodiment of the prosthetic components, indicated as 610, and as illustrated in FIGS. 15 and 27, the socket implant 612 is comprised of a metal segmented first shell 616, which receives a second shell 670 that is constructed from a single piece of metal, which then receives a synthetic resin cup 706. Again, the bore through the femur must be large enough to receive the single piece metal second shell.

As it is the most complex, the primary discussion will be directed to the preferred embodiment of the prosthetic components 10, as illustrated in FIGS. 1–13. This does not mean that this is an embodiment that is preferred over the other embodiments, as embodiments that are less complex are preferred, if the patient's bone structure is capable of receiving it. The socket implant 12 comprises a segmented first shell 16, which will be mounted into the prepared hip acetabulum. The segmented first shell 16 is comprised of a base 18 and a plurality of segments 20a–j that engage one another. The term segment is defined as a separate piece of something and segmented is defined as something that is comprised of separate pieces. Any convenient number of segments can be used; however, ten segments have been used for illustration purposes. Therefore the segmented first shell 16 is comprised of separate pieces or segments 20a–j that are joined together to form the segmented first shell 16. As seen more clearly in FIG. 4, the base 18 has at least one ridge 22 that is formed in the top surface 24 of the base 18 proximal to the edge 26 of the base 18 and projects outwardly therefrom. In a preferred embodiment, the ridge 22 is continuous; however, this is unnecessary as long as a portion of the ridge 22 engages each segment 20a–j. The base 18 has a hole 27 therethrough for receipt of a cannulated screw 29 for attachment of the base 18 to the hip bone. The bottom surface 28 of the base 18 is curved to fit the curvature of the prepared surface on the hip bone. A plurality of flexible secondary guide wires 30, one for each segment 20a–j, are threadably mounted to the ridge 22 so that they are spaced apart from one another.

Each segment 20a–j has an inner surface 32, an outer surface 34, a longitudinal first side 36, a longitudinal second side 38, a first end 40 and a second end 42. The outer surface 34 of each segment 20 is longitudinally and transversely arcuate, with a curvature that will match the curvature of the prepared surface of the hip. Each segment has a groove 44 formed in the outer surface 34 proximal the first end 40, as seen in FIG. 3 and FIG. 5, and a hole 46 that extends from the bottom of the groove to the inner surface 32. Two or more of the segments also have a hole 48 that extends through the inner and outer surfaces of the segment intermediate the first and second ends 40 and 42 of the segment. At least two of the holes 48 receive surgical nails 50 therethrough, one nail 50 being visible in FIG. 2, that are used to attach some of the segments 20a–j to the prepared bone surface.

As seen most clearly in FIG. 5, all but two of the segments 20a–j have the same interlocking lands and grooves which can be described as male and female. The segments 20a–g are identical each having a male arm 52 that extends outwardly from the first side 36 and then inwardly toward the longitudinal axis A of the shell 16. The arm 52 extends longitudinally from the second end 42 toward and proximal to the first end 40. A female second arm 54 extends outwardly from the second side 38 of each of the segments 20a–j and then away from the longitudinal axis A of the shell 16 to form a groove 58. The groove 58 is sized and configured to receive the land 56 of the male arm 52 to form a land and groove interlocking connection. Segment 20i is the last segment to be attached to adjoining segments, and therefore must be inserted from the inside as the shell is generally spherical in shape, and thus the interior of the shell has a smaller circumference than the exterior. Therefore segment 20i must be wedge shaped with the outer surface 34 being narrower than the inner surface 32. The adjacent sides of the two adjoining segments, 20h and 20j, also must be modified to receive the wedge shape of the segment 20i. In addition, segment 20i must have two female second arms 54 and the adjacent segment 20h must have two male first arms 52 to enable the last segment 20i to interlock with the adjacent segments completing the shell 16.

In a preferred embodiment of prosthetic components 10, the first shell 16 is constructed from titanium or cobalt chrome. In other preferred embodiments of prosthetic components 10, other materials that are very resistant to wear are suitable for the purpose.

In a preferred embodiment of prosthetic components 10, the shell 16 will be received by the surgeon in disassembled form for thorough disinfecting prior to assembly in the patient by the surgeon. During assembly of the first shell 16, each segment is mounted on a respective secondary guide wire 30 and advanced downwardly until the groove 44 engages the ridge 22 on the base 18. The secondary guide wires 30 guide their corresponding segments to their proper position. These wires must be very flexible to enable the segments to easily slide down the wire in the cramped space used during the surgery, to be described in greater detail below. After assembly of the shell, the flexible wires 30 are unscrewed from their threaded holes 59 and then removed. In another preferred embodiment, holes are bored all the way through the base 18 to provide a new hole 60. As seen in FIG. 4A, the first end 62 of a closed loop 64 of surgical thread, is passed through the hole 60 in the base 18 from the top downwardly. The second end 66 of the loop is then passed through the loop at the first end 62 to connect the thread to the base 18. The first end of the thread loop 66 is then passed through the hole 46 in one of the segments 20a–j. Once the segments 20a–j are in place, each of the plurality of loops of thread 64 are cut and the thread 64 is pulled from the base 18 through the hole 46 in the segments 20a–j.

Figures 8, 9, 10, 11:
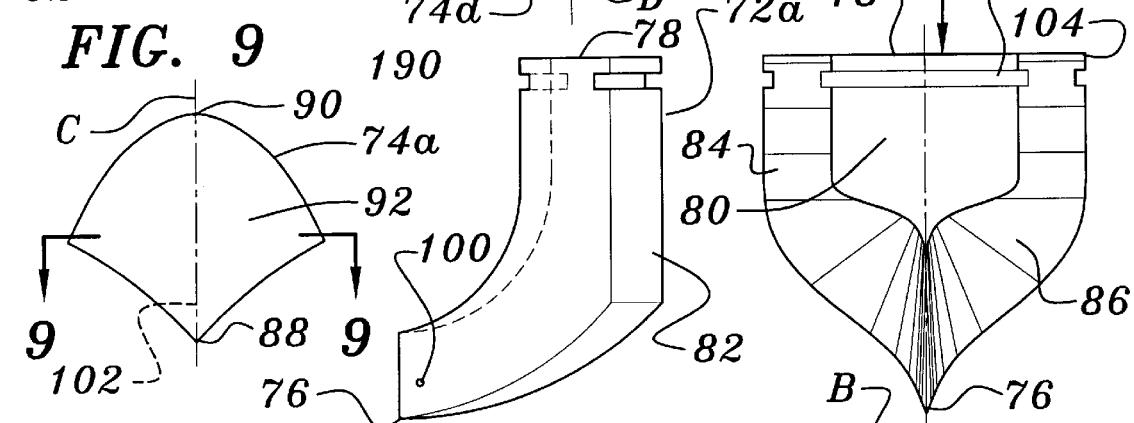
FIG. 8 is a detailed front elevational view of one of the second group of parts of the segmented shell of this invention.
FIG. 9 is a cross-sectional view taken along line 9—9 of FIG. 8.
FIG. 10 is a side elevational view of one of the first group of parts of the segmented second shell of FIG. 6.
FIG. 11 is a front elevational view of one of the first group of parts of the segmented second shell of this invention.

In a preferred embodiment of prosthetic components 10, a segmented second shell, shown generally as 70 in FIGS. 6–11, is sized and configured so that it can be assembled within the first segmented shell 16. The assembly will be discussed further below. The second shell 70 comprises a plurality of parts, those skilled in the art will easily be able to determine the suitable number of parts to be used for a particular patient. A total of 10 parts have been used for illustrative purposes, a first group of parts 72a–e and a second group of parts 74a–e. Each of the group of parts 72a–e have a longitudinal axis B, a first end 76, a second end 78, a first face 80, a second face 82, a first side 84 and a second side 86. Each of the second group of parts 74a–e have a longitudinal axis C, a first end 88, a second end 90, a first face 92, a second face 94, a first side 96, and a second side 98. The first face 80 and the second face 82 of the first group of parts and the first face 92 and the second face 94 of the second group of parts are each longitudinally and transversely arcuate. The first ends 76 and 88 of each part of the first and second group of parts is linked to one another, preferably by surgical thread passing through the hole 100 in the parts 72a–e and the hole 102 in the parts 74a–e, as seen in FIGS. 10 and 8 respectively.

A portion of the sides 84 and 86 of each of the parts 72a–d, that is proximal the outer rim 104 of the shell 70 extend radially toward the central axis D. When the parts 74a–e are being assembled to form the cup shaped shell 70, the last part 72e must be tapered outwardly so that the sides 84 and 86 are angled toward one another and thus the horizontal arc of the second face 82 is smaller than the horizontal arc of the first face 80. To ensure that all sides fit tightly, the sides of the adjacent parts, 72a and 72d, must be tapered inwardly to match the taper of part 72e so that the sides fit tightly when the parts are fully assembled.

Figure 6:
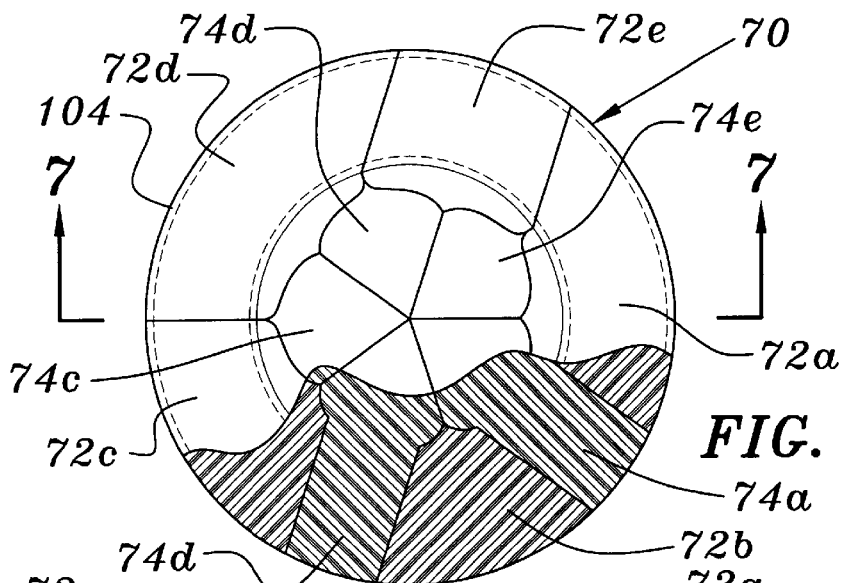
FIG. 6 is a top plan view of the segmented second shell of this invention with a portion cutaway in cross-section to illustrate the relationship of the parts.

The sides 84 and 86 of each of the parts 74a–d are tapered outwardly so that the first face 92 is much larger than the second face 94. The transverse dimensions of the second face 94 of the parts 74a–d vary along the longitudinal axis C between the first end 88 and the second end 90. The horizontal width of the second face 94 varies from a sharp edge (where the cross-section of the part would be triangular) proximal the first end 88 to a greater cross-section as seen in FIG. 9 and then narrows proximal the second end 90 to a generally triangular cross-section. As each of the parts 74a–e is inserted between adjoining parts 72a–e, as seen in FIG. 6, the curvatures of the adjacent sides must match one another to make a tight friction fit. The segmented second shell 70 may be constructed from synthetic resin or a suitable metal.

In a preferred embodiment of the prosthetic component 10, the segmented second shell 70 may be made using the same structure used for the first segmented shell 16, discussed above. This structure, using a base having threaded guide wires and interlocking segments will be just as satisfactory a structure as the second segmented shell 70 having a first group of parts 72a–e and a second group of parts 74a–e. The primary difference will be that the second shell will be smaller than the first shell and made from a suitable synthetic resin or metal. The second shell when made of metal will be attached to the first segmented shell 16 by snap rings, and when made of synthetic resin the second shell will be attached to the first segmented shell 16 by heat and pressure or by snap rings.

As shown in FIG. 2, a cup 106 is inserted within the second shell 70, which is preferably made of solid titanium or cobalt chrome with a very polished interior surface 108. The metal cup is used when the second shell 70 is constructed from synthetic resin. In other preferred embodiments of the prosthetic components 10, the cup 106 may be constructed from a synthetic resin, particularly when the second shell 70 is constructed from metal. When constructed from a synthetic resin, the cup 106 may be formed so that when the cup 106 receives the ball 110, the edge 112 of the cup 106 extends beyond the equator of the ball 110 so that the cup 106 snaps onto and is retained on the ball 110 for easy insertion into the socket implant 12. The cup 106 may be attached to the second shell 70 by a snap ring.

Figure 7:
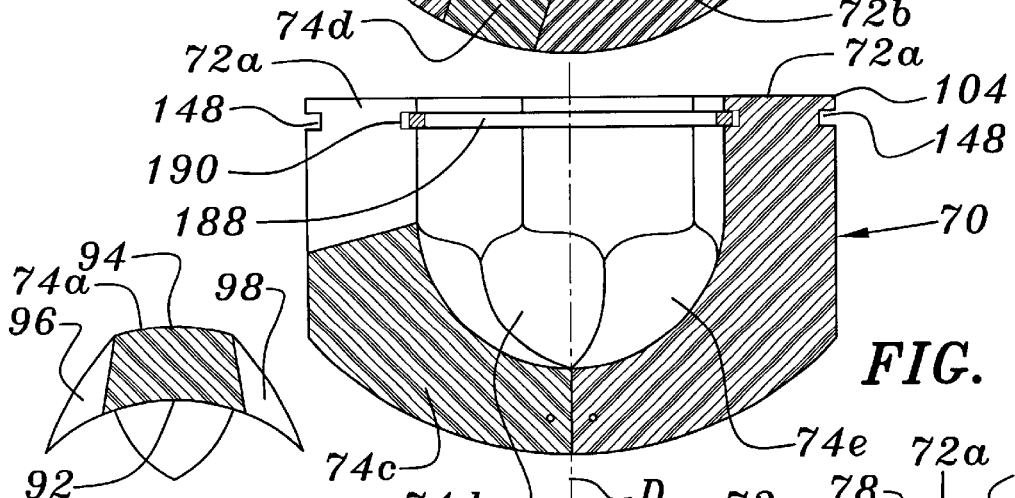
FIG. 7 is a cross-sectional elevational view taken along line 7—7 of FIG. 6.
Figure 25:
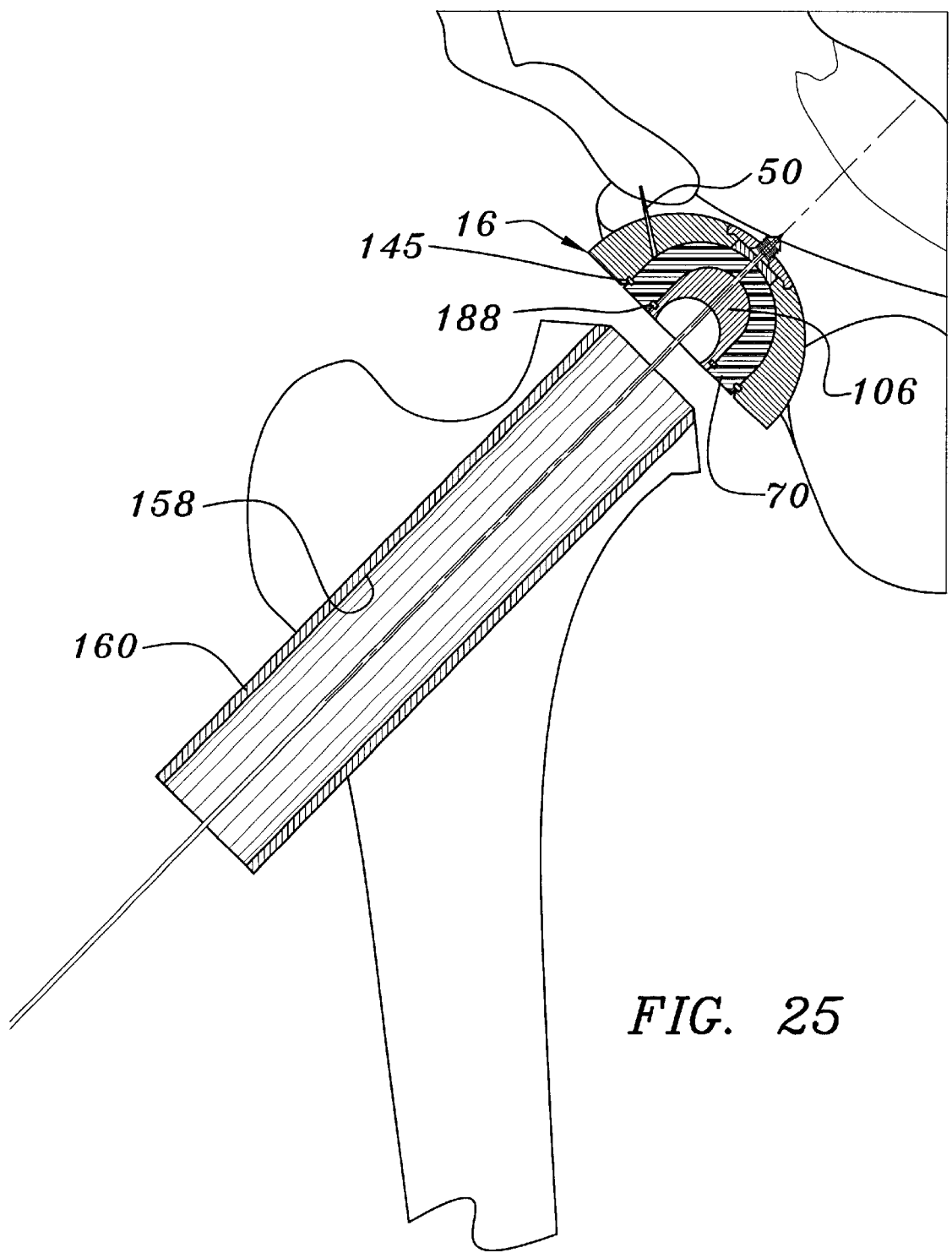
FIG. 25 illustrates the placement of the cup into the first and second segmented shells of FIG. 24.

The shells and the cup may be attached to one another in a number of different ways. Snap rings or drop rings operate simply. Snap ring or drop ring 145, as seen in FIG. 25, is inserted within a groove 146, as seen in FIG. 5 that matches a second groove 148 in the second shell 70, as seen in FIG. 7. When the second shell 70 is pressed into place, the snap ring 145 is expands into the groove 146 so that when the groove 146 aligns with the groove 148 the snap ring shrinks into the groove 148 locking the two shells together. Snap ring 188 in groove 190 may engage the groove 182 in the cup 106. When a plastic cup or plastic segmented shell is to be attached to an inner metal shell, heat (approximately 400 degrees) and pressure can be applied to the plastic cup or shell so that it bonds to the roughened surface of the metal shell. In other embodiments, it is possible to use well-known biologically tolerable bonding resins for that purpose.

The ball implant 14, conveniently shaft 114, as shown in FIGS. 12 and 13, has a first end 116 and a second end 118. The shaft 114 is comprised of the ball 110, a body 120, and a neck 122 that attaches the ball 110 to the body 120. The ball 110 is generally spherical and is comprised of highly polished titanium or cobalt chrome. The neck 122 and the body are comprised of steel and the body 120 is coated with any one of the well-known ingrowth surfaces for encouraging the growth of the bone to that surface for bonding the body 120 to the adjacent bone of the femur. The shaft 114 is cannulated, having at least one tube 124 that extends from an open first end 126 at the bottom 128 of the shaft 114 to an open second end 130 at the neck 122. The tube 124 is used to flush and suction the site of the hip joint to remove debris that may have collected in the joint area due to the wear of the head 110 or cup 106 and may also be used to insert antibiotics to fight infection that may occur after implantation of the prosthetic components 10. A bag constructed from a formulation of silicon and rubber (or other material that is non toxic to the surrounding tissues) may be implanted in the patient's leg adjacent the second end 118 of the shaft 114 and attached by well known means to the shaft 114 so that it is in fluid flow communication with the tube or tubes 124. The bag will collect debris created by the prosthetic joint to prevent the debris from a toxic interaction with the surrounding tissue. An open second tube 132 also extends inwardly from the bottom of the shaft 114 to a closed second end 133 proximal the neck 122. The second tube 132 has an open first end 134 that is threaded for attachment of a syringe through which a cement may be injected into the tube 132 to bond the body 120 to the surrounding bone. The threads on the second tube 132 may also be used for attachment of an extraction tool (not shown) to remove the shaft 114, if that should be necessary. At least one secondary tube 136 is connected at one point along the second tube 132 and is in fluid flow communication therewith. The secondary tube 136 extends through the side wall 137 of the body 120 so that cement may be applied between the body 120 and the surrounding bone. For an even distribution of the cement around the body 120, a plurality of secondary tubes 136 interconnect with the second tube 132. For a more even distribution along the longitudinal length of the body 120, a second set of secondary tubes 136' may interconnect in fluid flow communication with the tube 132 to apply cement closer to the neck 122. In the preferred embodiment illustrated in FIGS. 12 and 13, two tubes 124 are formed in the shaft 114. The body 120 has also been pre-bored to receive one or more screws 138 for attachment to the bone of the femur. As shown in FIG. 2, the screws may have expandable ends 188 for a firmer attachment to the bone, which is particularly desirable if the bone is soft.

A groove 140 is formed in the side wall 137 adjacent the bottom 128 to receive a U-shaped shield 142 that has a pair of legs 144 that extend outwardly from the groove. This shield is curved to fit the body 120 so that the legs will engage the corner of the cortical bone along the superior portion of the hole through the femur to reduce the risk that the bone will fail due to stresses applied by the body 120 of the shaft 114.

As discussed previously, when the patient's bone structure is large enough, a second preferred embodiment, prosthetic components 310, should be used, as illustrated in FIGS. 14, 22 and 23. In preferred embodiment 310, it was possible to insert thicker segments 420a–j (not all of which are shown) than those shown in FIG. 4, eliminating the need for inserting a second shell. Therefore the socket implant 312 comprises the segments 420a–j that are joined to one another to form the first shell 316 and a cup 406. The cup 406 is sized and configured to be received into the interior cavity of the first shell 416. The cup 406 is held in the first shell 416 by the snap ring 445. The cup 406 may be constructed from metal or from synthetic resin. Attachment by a snap ring may be done whether the cup 406 is metal or synthetic resin. The socket implant 312, is now completed. The shaft 414 is very similar in size and shape as shaft 114, described above, and the cup 406 will be sized to receive the ball 410 therein, which is generally the same size as ball 110.

The third preferred embodiment, prosthetic components 610, illustrated in FIGS. 15 and 27 are very similar in structure to the second preferred embodiment, prosthetic components 310, except a solid second shell has been inserted between the first segmented shell 616 and the cup 706. As shown in FIG. 15, the second shell 670 is formed as a single piece, that is, not segmented, as previously defined. The single piece shell 670 would have the same general shape as the segmented shell 70. The only limitation is that the diameter of the shell 670, at its maximum diameter, must be less than the diameter of the sleeve (not shown), which will be discussed further below. The second shell 670 is preferably made from metal, titanium or cobalt chrome. A synthetic resin cup 706 is inserted in the second shell 670 and attached by snap rings or heat and pressure as previously discussed. In this third preferred embodiment, the shaft 714 is very similar in structure to the shaft 114, and the cup 706 is sized to receive the shaft 714.

Having thus set forth a preferred construction for the current invention, is to the remembered that this is but a preferred embodiment. Attention is now invited to the use and the method for placement of the prosthetic implant of this invention.

These prosthetic components are used for surgical implantation when the patient is able to withstand a longer recovery period than that typically required by prior art methods. Recovery, in this case, may require the patient to be on crutches for a number of months to ensure complete healing before placing stress on the joint. An advantage of this apparatus and method is that the surgery is much less invasive, takes much less time, requires much less surgical support in the operating room, and is much less expensive. In addition, if these components were to fail, a full hip joint replacement, done in accordance with current practice, is still available, as more than enough of the femur remains and only a small portion of the acetabulum was removed. The steps for implantation of these prosthetic components are discussed below.

Figure 16:
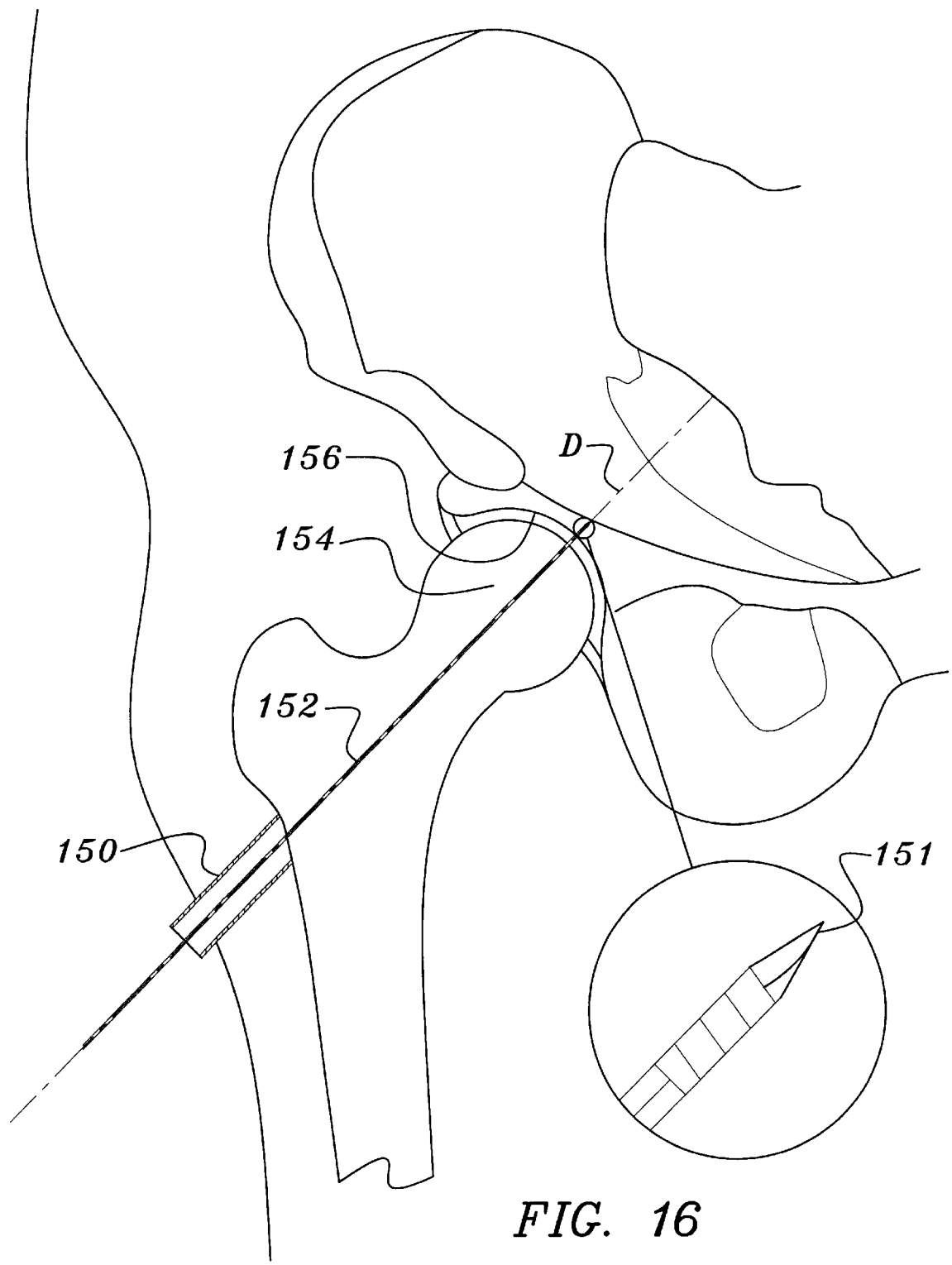
FIG. 16 is a detailed view of the hip structure illustrating the placement of the guide wire into the hip bone.
Figure 17:
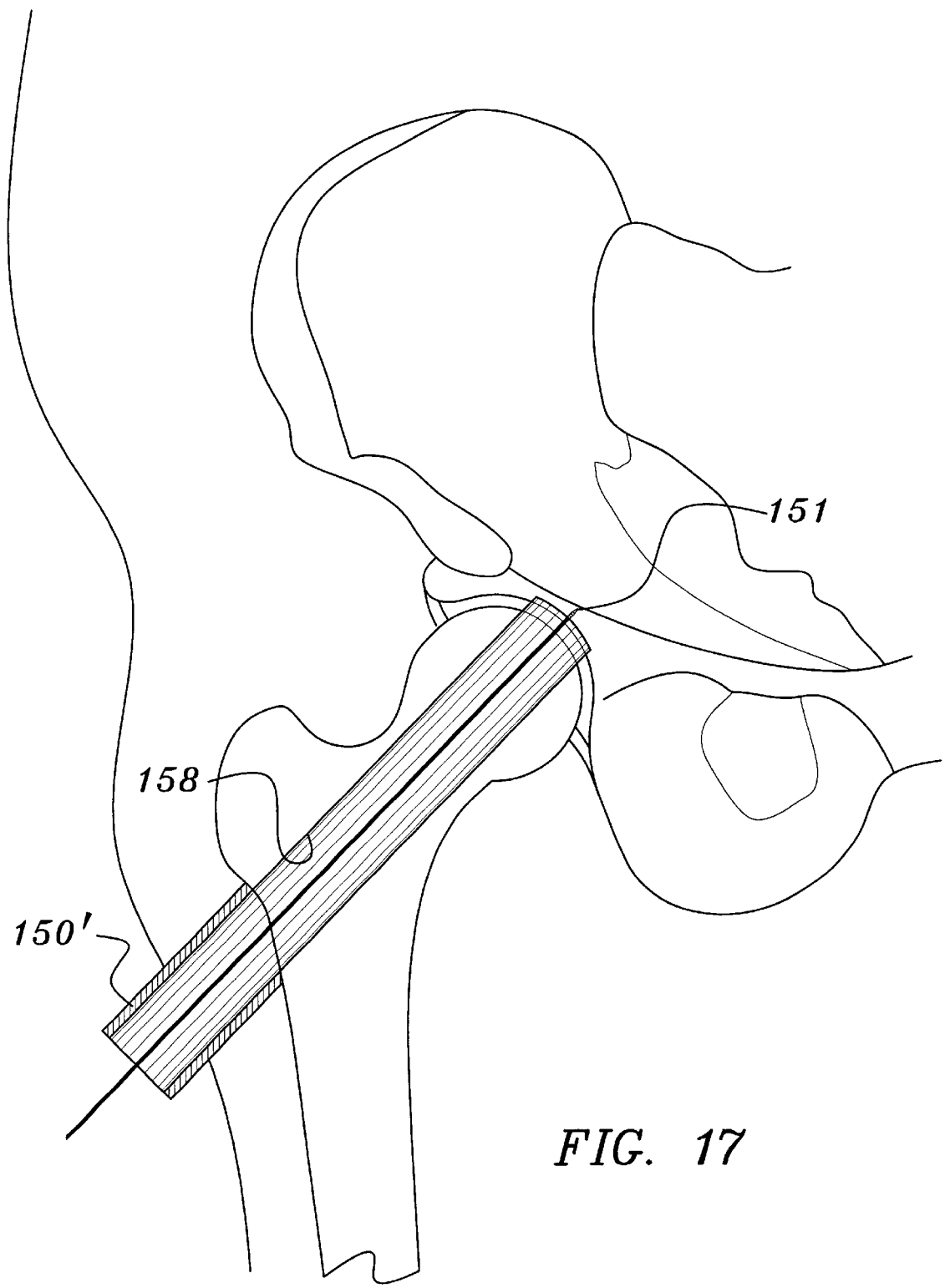
FIG. 17 illustrates the placement of a protective hollow blunt guide and the hole bored through the neck and head of the femur and into the acetabulum of the hip bone.
Figure 34:
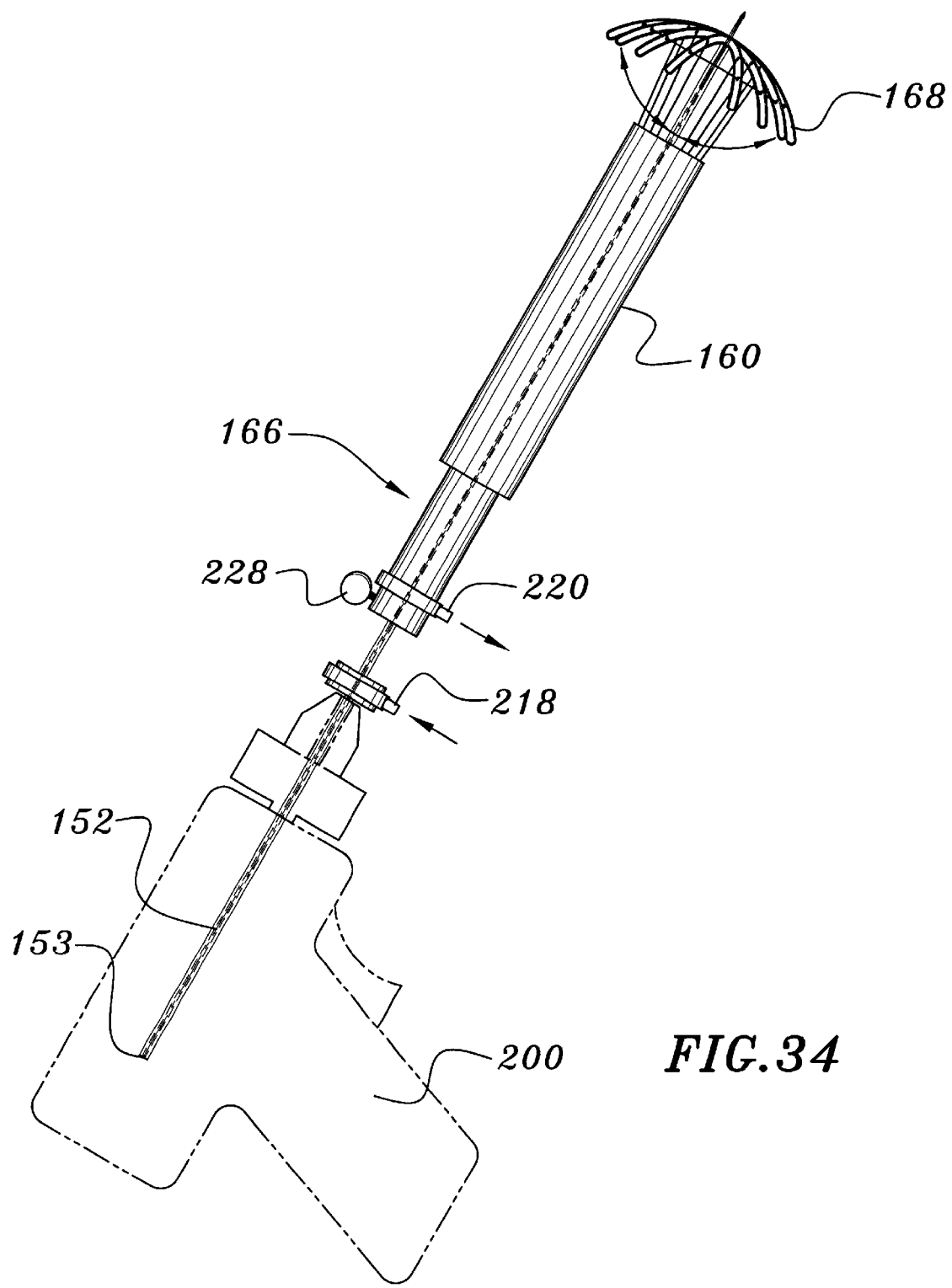
FIG. 34 illustrates the attachment of the expandable drill bit to a drill motor for rotation of the expandable drill bit.

The patient is suitably prepared for surgery in accordance with known practice. The patient's body is aligned so that a longitudinal axis D extending from and neck and head of the femur of the patient passes through the geometric center of the acetabulum of the patient. The patient's body is placed in skin traction to prevent movement during surgery. A one inch incision is made to expose the femur at the point at which the longitudinal axis exits the femur, just under the greater trochanter. As seen in FIG. 16, a hollow and blunt guide 150 is inserted up against the bone so that its axis is coincident with the longitudinal axis D. A 2 mm smooth guide wire 152 with a threaded tip is passed through the guide 150 and along the longitudinal axis D so that the guide wire 152 is aligned with and driven through the geometric center of the femoral head, across the joint and into the geometric center of the acetabulum 156. A cannulated drill bit is mounted over the guide wire 152 and a hole is bored through the femur, the neck of the femur, the head, across the joint and 2 mm into the acetabulum. A larger blunt guide 150' is placed over the smaller blunt guide 150, which is then removed. A second cannulated drill bit may be inserted in the drill to bring the hole 158 to the proper diameter, as shown in FIG. 17. The size of the hole 158 will largely be determined by the size of the femur neck. The hole 158 must not remove the interior of the subchondral plate. To ensure that the bore does not extend beyond the planned depth into the acetabulum, usually 2 mm, the cannulated drill bit and drill ride the guide wire 152 to a stop 153, as seen in FIG. 31. FIG. 34 demonstrates use of the drill motor 200 with the expandable drill bit 166; however a cannulated surgical drill bit may be inserted in the drill motor 200 and controlled in this manner. That is, the guide wire 152 is received within a tube in the drill motor 200 that has a predetermined length. The guide wire 152 is sized so that when the end of the guide wire 152 reaches the end of the tube, or stop 153, the proper length of the hole 158 has been reached.

Figure 18:
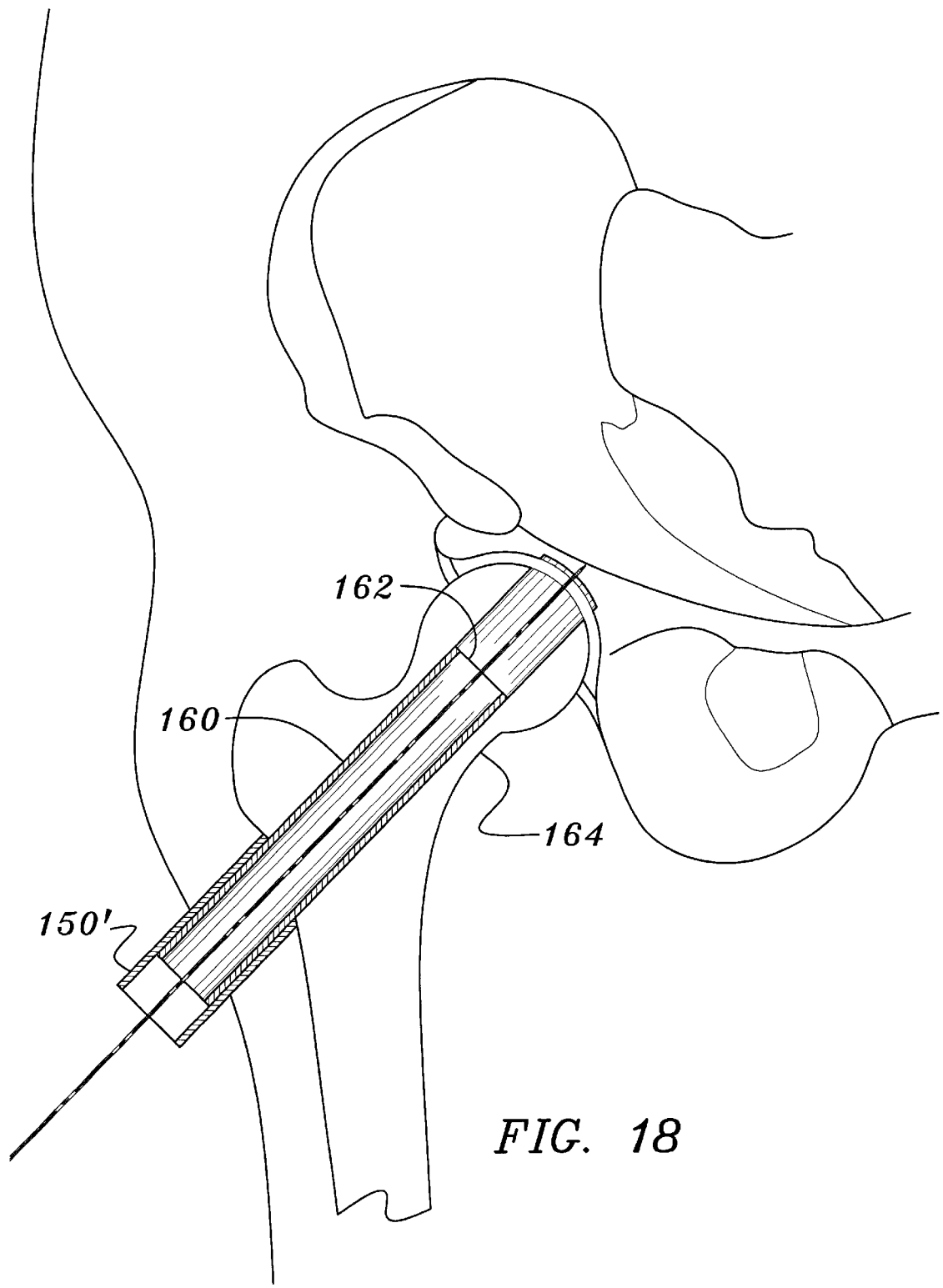
FIG. 18 illustrates the placement of a sleeve into the hole bored through the femur.
Figure 19:
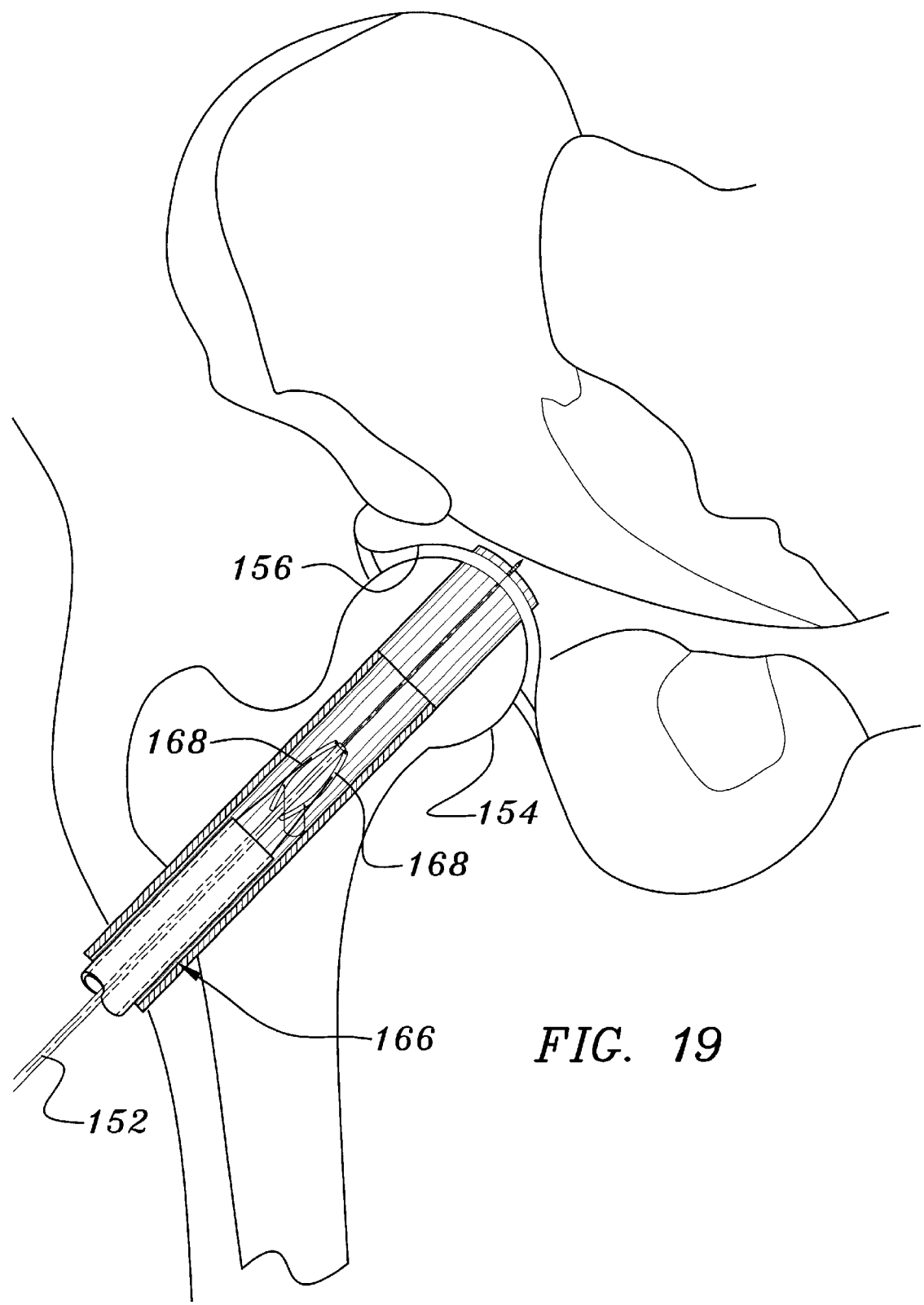
FIG. 19 illustrates the insertion of the expandable bit into the sleeve.
Figure 20:
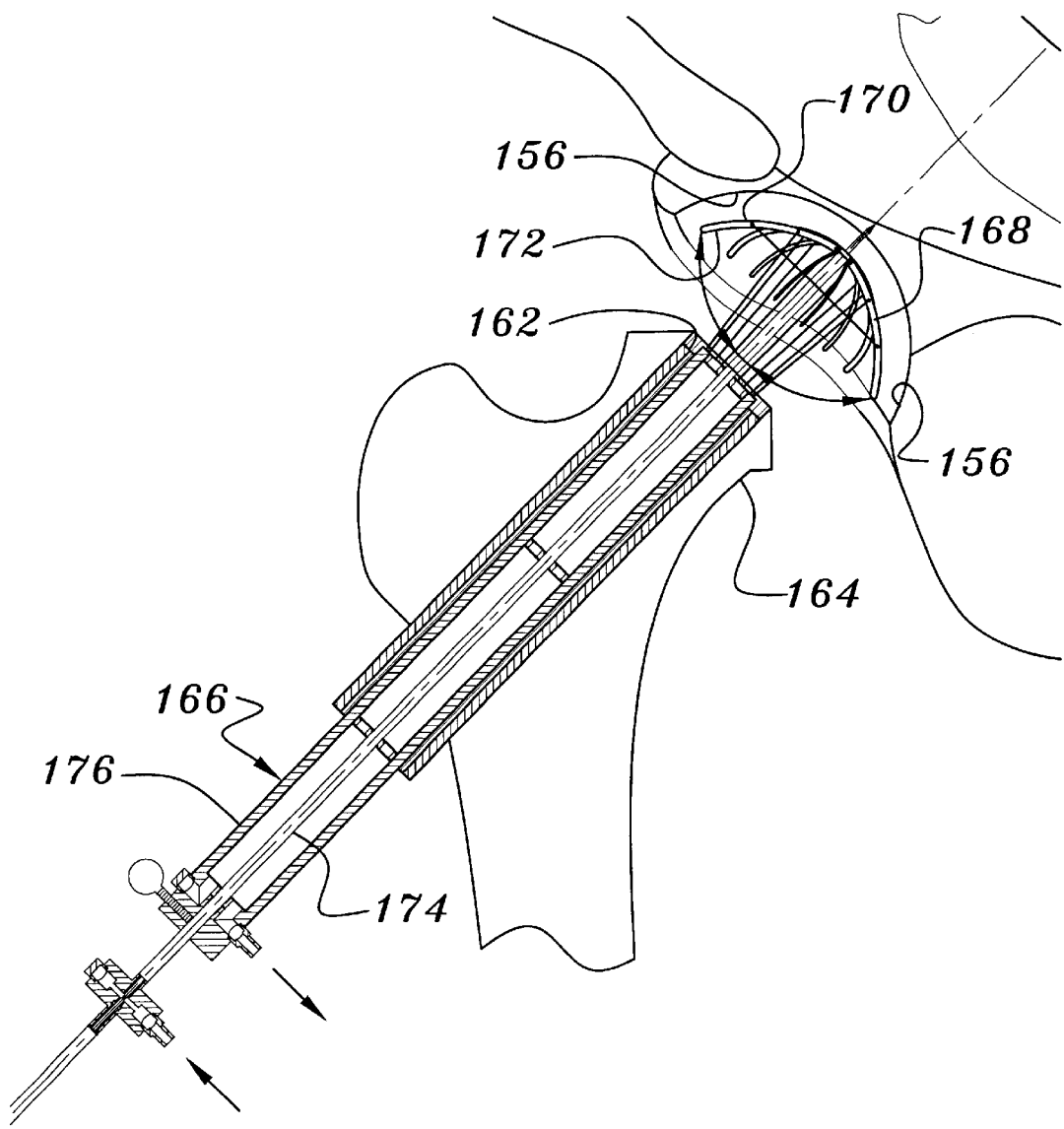
FIG. 20 illustrates the extension and expansion of the expandable bit for removal of a portion of the acetabulum of the hip bone.

As seen in FIG. 18, sleeve 160, having the same exterior diameter of the hole 158 bored in the femur, is now placed around the wire and inserted through the blunt guide 150' and into the femur until the first end 162 of the sleeve 160 lies proximal the neck 164. The blunt guide 150' is then removed. An expandable drill bit 166, which will be discussed in greater detail below, is mounted on the guide wire 152 and inserted into the sleeve 160, as shown in FIG. 19. This drill has multiple blades 168 that can be expanded so that the outer cutting edges 170 of the blades 168, when fully expanded, match the spherical shape of the acetabulum. As seen in FIG. 20, once the blades have exited the sleeve 160 they begin cutting away the head of the femur 154. The expandable drill bit 166 is advanced until the drill blades 168 remove approximately 2 mm of the acetabulum 156. The expandable drill bit 166 includes means for measuring the distance that has been bored. Once the predetermined distance for movement of the drill along the guide wire has been reached the expandable drill bit 166 is drawn inwardly so that the inner cutting edge 172 of the blades 168 can remove additional portions of the head 154 of the femur that must be removed to ensure adequate clearance for full movement of the mechanical joint. The expandable drill bit 166 is advanced again until the blades 168 can be closed and then the expandable drill bit 166 is retracted through the sleeve 160. The drilling operation is rigidly controlled through fluoroscopy. While drilling is being accomplished a flushing fluid is injected into the site through a tube 174 in the expandable drill bit 166 and suction is applied to the central portion of expandable drill bit 176 for removal of debris.

Once the site has been cleaned of debris, a socket implant 12 is attached to the hipbone of the patient. The ball 110 is much smaller than the head of the femur, so that it can be inserted through the hole 158 through the femur, and the acetabulum site on the hipbone has been enlarged by the expandable drill bit 166. Therefore, the cup 106 receiving the ball must be much smaller, requiring a support structure between the hipbone and the cup 106 of the socket. The larger the cross-section of the neck of the femur the larger the hole 158 that can be bored through the femur, without damage to the subchondral plate, through which the socket implant is passed. The surgeon, based upon measurements of the patient's bone structure, will determine the particular size and structure of the socket implant. In the previous discussion of the preferred embodiments of the socket implant 12, three preferred embodiments of the prosthetic components, 10, 310 and 610 were discussed. A first preferred embodiment, prosthetic components 10, comprises a segmented first shell 16, a segmented second shell 70, and a solid synthetic resin or metal cup 106 and a shaft 114 as seen in FIG. 1. A second preferred embodiment, prosthetic components 310, comprise a socket implant 312 comprised of a metallic segmented first shell 316 and a metallic or synthetic resin cup 406, as seen in FIG. 14. A third preferred embodiment, prosthetic components 610, comprise the segmented first shell 616, a single piece metal second shell 670, and the cup 706, as seen in FIG. 15. Certainly, the less parts needed to complete the socket implant, the easier the placement and the more quickly the operation can proceed, which is better for the surgeon and the patient.

With the site prepared, and the surgeon having selected the first embodiment of the prosthetic components 10, the next step is to implant the segmented first shell 16. The base 18 having the cannulated screw 178 inserted therein, is mounted on the guide wire 152 so that the cannulated screw and base 18 passes along the guide wire 152 and is therefore centered in the acetabulum. With the base 18 centered by the guide wire the self-tapping cannulated screw 29 is driven into the bone of the acetabulum of the patient by a cannulated screw driver. The ends of the plurality of flexible wires 30 attached to the base 18 extend outwardly through and beyond the sleeve 160. The first segment to be implanted must be the segment having the two male arms 52, which in FIG. 5 is segment 20h. A flexible secondary guide wire 30 is received through the hole 46 in the first segment 20h so that the segment 28 is slid downwardly on the guide wire until the groove 44 on the first segment 20h engages the ridge 22 of the base 18, as seen in FIGS. 4 and 5. Once the segment is seated in place a surgical nail 50 is driven through the hole 48 in the segment 20h to attach the segment 20h to the hip bone. As seen in FIG. 19, some of the segments are already in place and one segment is shown mounted on one of the flexible secondary guide wires 30, so that the flexible secondary guide wire 30 passes through the hole 46 in the segment.

Figure 21:
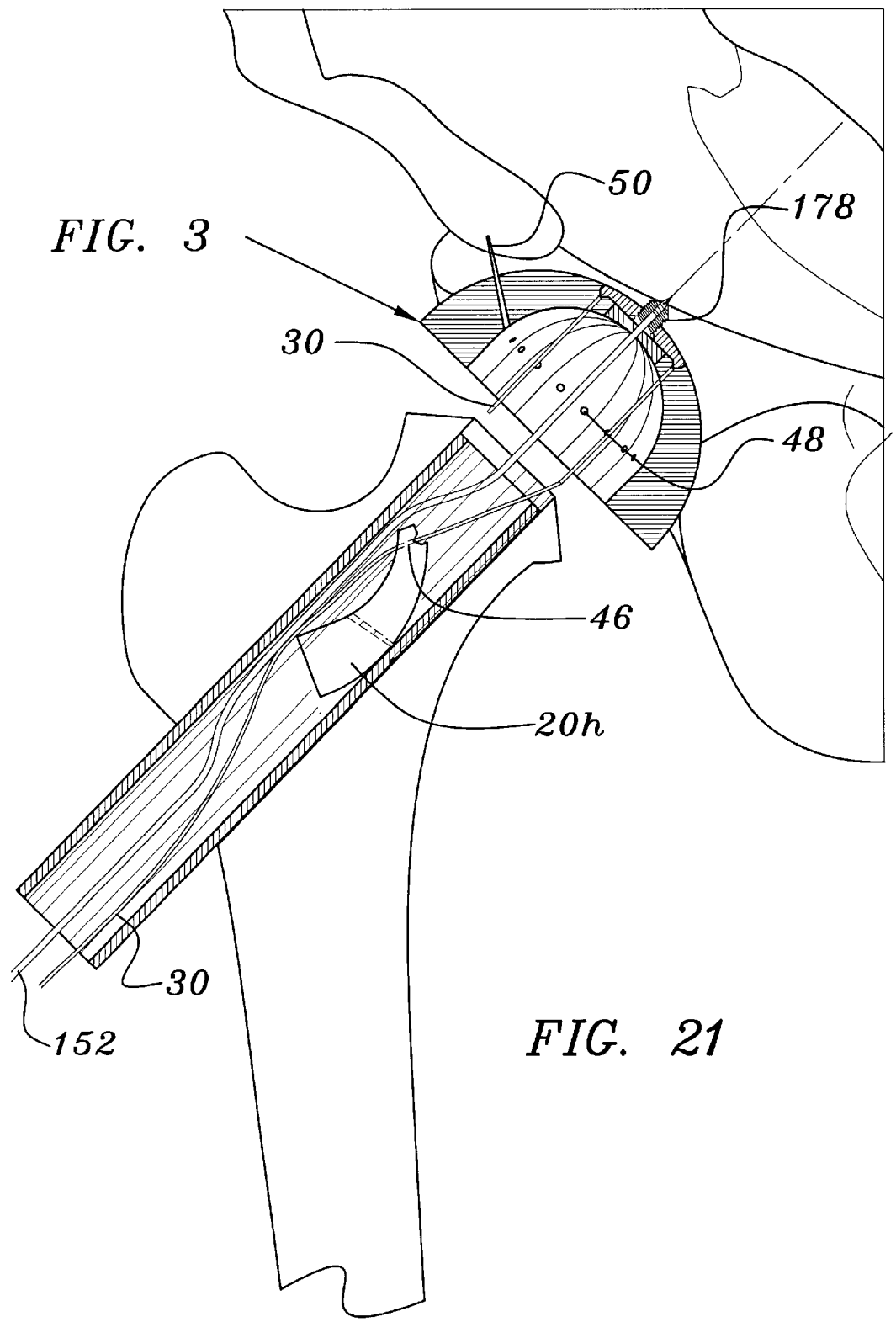
FIG. 21 illustrates the placement of a segmented first shell and transportation of one of the plurality of segments through the sleeve guided by a secondary guide wire for placement onto the base and engagement with an adjacent segment.

The next segment 20g is then mounted on its corresponding flexible secondary guide wire 30 and installed so that the female land 56 engages the groove 58 of the segment 20h. The next segments are inserted in the same manner until the next to last segment 20j is in place. The last segment, segment 20i, has two female arms 54 that engage with the male arms 52 on segments 20h and 20j interlocking the segments 20a–j of the segmented first shell 16 in place. In addition, as discussed previously, the segment 20i is tapered so that it may be inserted in place from the inside of the first shell 16. A surgical nail is driven through the hole 48 of segment 20i to lock the segments together. As seen in FIG. 21, surgical nails may be driven in more of the holes 48 in the segments 20a–j if the surgeon believes it is necessary. The location of the nails will be determined by the surgeon based upon the thickness and density of the bone in the adjacent area; however, they usually may be driven into the superior, posterior superior or the straight posterior portions of the hipbone. Certainly segments 20h and 20i should be located adjacent to bone that is thick and dense so that surgical nails 50 may be driven through these key segments. While FIG. 21 illustrates the method for placement of a segment, it also illustrates the completed implantation of the first segmented shell 16, with the plug 180 screwed into place, which, obviously could not happen until all the segments were in place.

As discussed previously, in another preferred embodiment a loop of surgical thread 64, as shown in FIG. 4A, may be used to guide the segments to their proper location. Certainly surgical thread is more flexible than wire and may create less difficulty in the installation of the segments.

Figure 24:
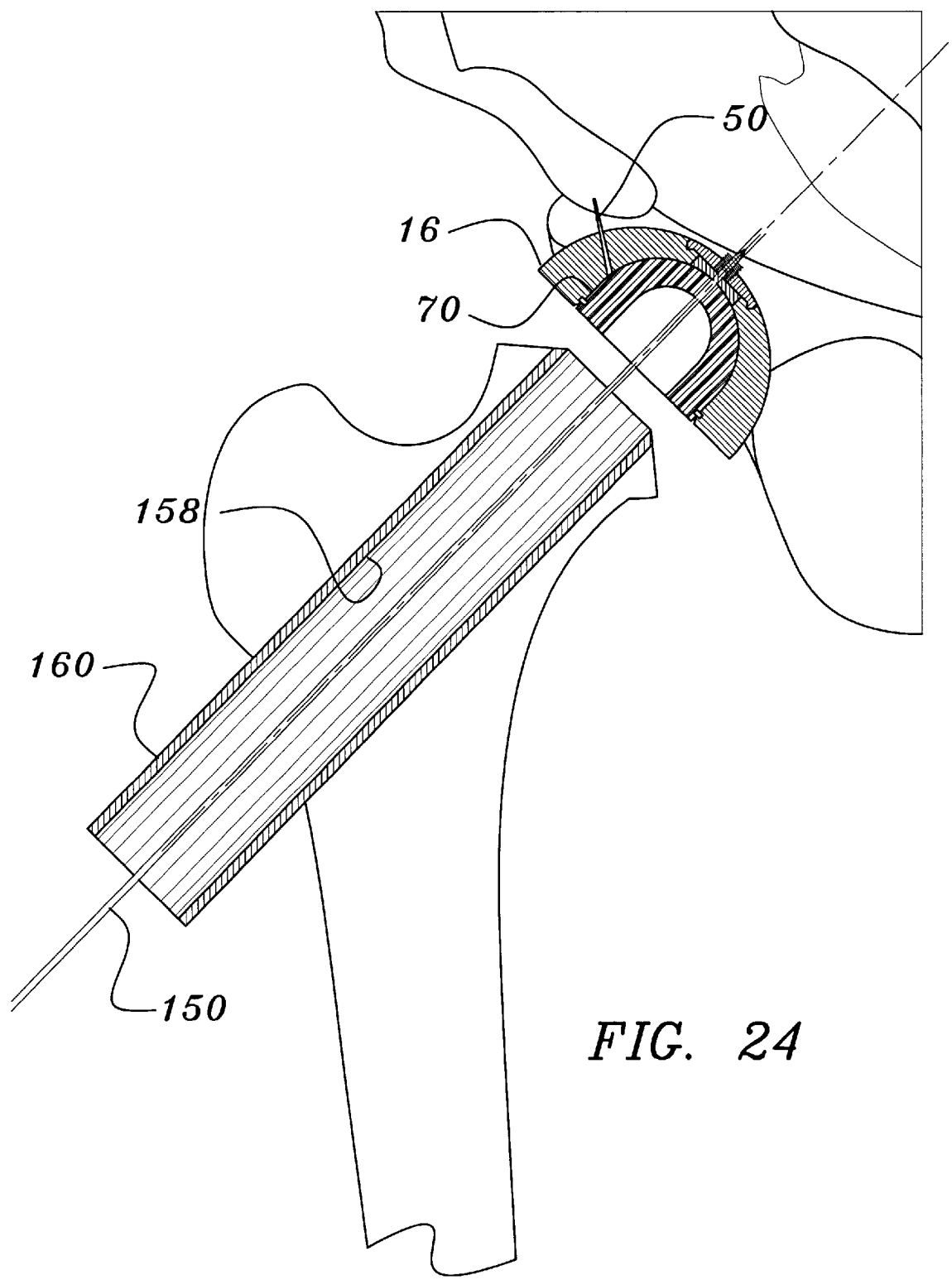
FIG. 24 illustrates the placement of a first segmented shell having thin segments and a second segmented shell.

The surgeon has selected the prosthetic components 10 as the size of the femur is average or small, and the segments of the first shell 16 will need to be small enough to pass through the hole 158 in the femur. In this case, it will be necessary to place the segmented second shell 70 within the first shell 16 to fill the space formed in the acetabulum of the patient to support ball 110, which is much smaller than the head of the femur. FIG. 24 illustrates the implantation of such a preferred embodiment with a segmented second shell 70 having been inserted within the segmented first shell 16.

Figure 26:
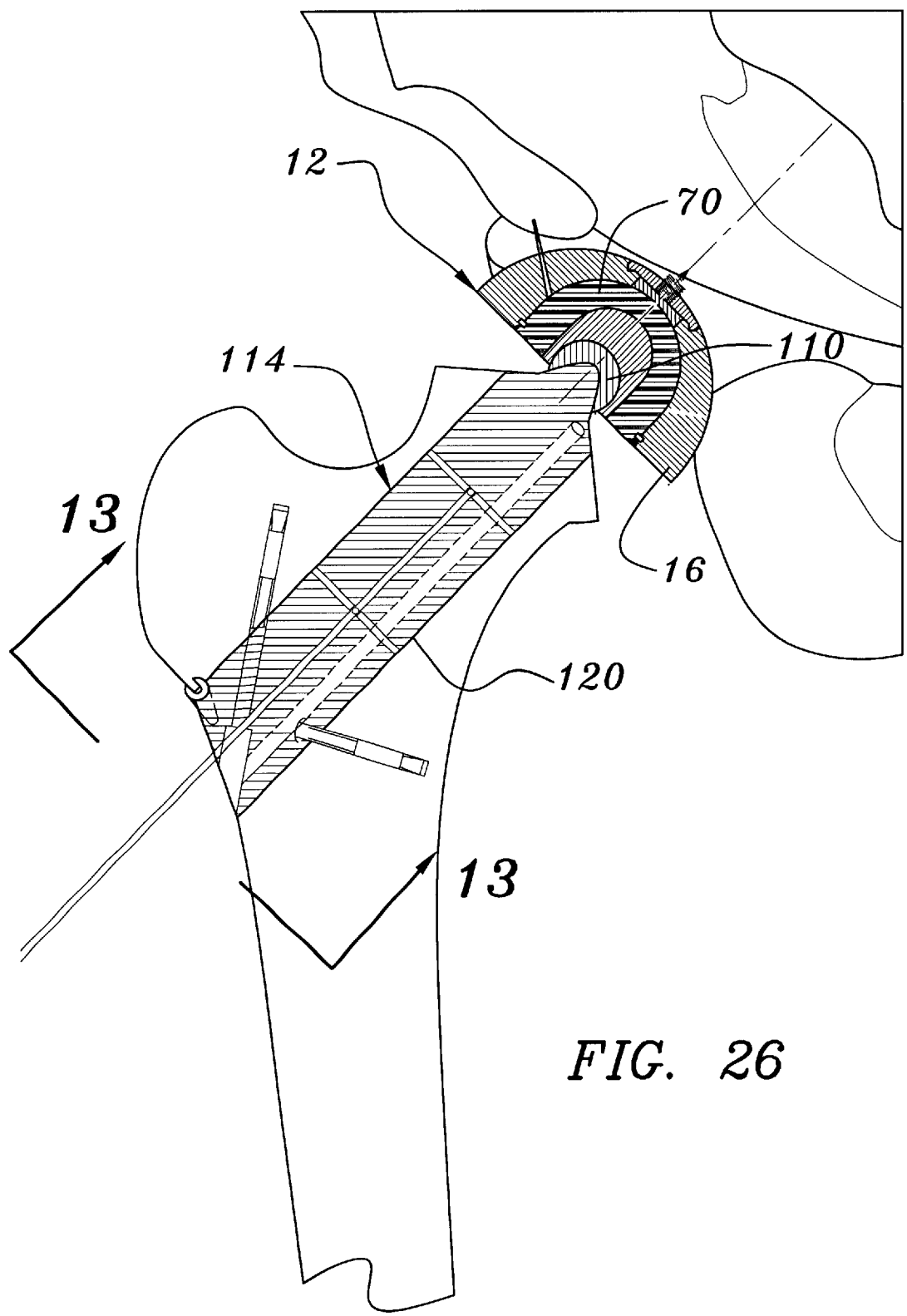
FIG. 26 illustrates the placement of the shaft into the hole through the femur and engagement of the ball with the cup of FIG. 25.

As shown in FIGS. 24–26, the second shell 70 lies between the first shell 16 and the cup 106 and is segmented. As shown in FIGS. 6–11, in a preferred embodiment, the segmented second shell 70 comprises a plurality of parts, a first group of parts 72a–e and a second group of parts 74a–e. The first group of parts 74a–e each have a hole 100 therethrough and the second group of parts each have a hole 102 therethrough. The parts are alternatingly strung on a surgical thread that is passed through the holes 100 and 102 and tied in a loop. The parts are then inserted through the sleeve 160 so that the guide wire 152 passes through the loop of surgical thread. The surgeon places the first group of parts within the first shell 16 beginning with part 72a and ending with part 72e. The last part 72e is tapered to provide a friction fit between part 72d and 72a, forcing the other parts into position forming a cup-shaped shell. The second group of parts 74a through 74e, which are held in proper orientation by the surgical thread, are then each inserted between the adjacent pair of the first group of parts 72a–72e. As seen in FIGS. 6 and 9, the second group of parts are tapered and may be readily placed in position and then firmly pushed into place. The parts 72a–e and 74a–e are then placed under pressure and high temperature (approximately 400 degrees), thereby bonding the plurality of parts 72a–e and 74a–e to one another and to the first shell 16.

When the second segmented shell 70 has the same configuration as the first segmented shell 16, it will be inserted through the sleeve 160 and assembled in the first segmented shell 16 in the same manner that the first segmented shell 16 was inserted through the sleeve 160 and assembled in the acetabulum. Of course, the first and last segments of the second shell will be preferably tacked to the first shell 16 to permit the attachment of the second shell to the first shell by heat and pressure or by a snap ring.

The next step is to insert a cup 106 through the sleeve 160 and attach it to the second shell 70 by a snap ring 188 that is inserted in the groove 190 in the parts 72a–e. As the cup is pushed into the interior cavity of the first shell 16, the exterior sides of the cup 106 engage the snap ring 188 pushing it into the groove 190 until the groove 190 aligns with the groove 182 in the cup 106, at which time the snap ring 188 expands outwardly and engages the groove 182 locking the cup 106 within the second shell 70, as seen in FIG. 25. The cup 106 may be constructed from metal or from synthetic resin. Attachment by a snap ring may be done whether the cup 106 is metal or synthetic resin; however, if the cup is made from synthetic resin it may be installed on the ball 110 prior to the shaft 114 being inserted in the hole 158, so that as the shaft 114 is pressed into the hole in the femur the ball 110 with the cup attached seats the cup 106 in the second shell 70 and is locked therein by a snap ring. As discussed previously the plastic cup 106 snaps on the ball as the edge 112 of the synthetic resin cup curves around the ball beyond its equator. The prosthetic acetabulum, or socket implant 12, is now completed.

The sleeve 160 is then removed from the hole 158, and as shown in FIG. 23, the shaft 114 is implanted in the femur of the patient. The shaft 114 is driven into the hole 158 so that the ball 110 is seated within the cup 106 for free movement between the ball and the cup. As the shaft 114 is inserted, a shield 142 is placed around the superior portion of the hole 158 and is held in place by the groove 140 formed in the body 120. To stabilize the shaft 114 during the healing process, at least one surgical screw 138 is inserted through a hole 184 in the shaft 114. The surgical screw 138 has a first end 186 that is capable of expanding after it has entered into the femur to more tightly hold the shaft 114 in place. This is particularly necessary if the bones are soft. Additional screws may also be inserted through two other holes 184, as shown in FIG. 13. If the patient has very soft bones due to osteoporosis, a syringe is threadably attached to the tube 132 and a fluid cement is forced into the tube 132 and out the secondary tubes 136 and 136' between the hipbone and the sidewall 137 of the body 120. Also, if the bones are soft a shaft with a larger diameter may be driven into the femur for a better bond, as long as the subchondral plate of the bone, the hard exterior layer of bone, is drilled to the size of the shaft.

The shaft 114 is cannulated by at least one tube 124 which permits flushing and suctioning of the hip joint site prior to closing the incision and at a later date, if infection or other difficulties occur. At this time, the surgeon may attach and implant a drainage bag constructed from a formulation of silicon and rubber, not shown, to catch any drainage after the incision is closed. The incision may now be closed. At a later date it may be necessary to remove and replace the drainage bag.

If the surgeon determines, through measurements of the patient's bone structure, that the bone structure can support the prosthetic component 310, the surgeon will normally select the prosthetic component 310 as it comprises fewer parts, thereby reducing the complexity of the operation. The steps for implantation of the prosthetic component 310 will largely be the same as the steps for implantation of prosthetic component 10, as described above. In this case, larger individual segments and possibly a greater number of segments will permit the much thicker segments of the first shell 316, as seen in FIG. 22, to be inserted through the sleeve 460. All the steps leading up to and for installing the first segment 316 are the same as described above. The thicker first shell 316 eliminates the need for installing a second segmented shell as contained in the prosthetic component 10.

The next step is to insert a cup 406 through the sleeve 460, the cup being sized and configured to be received into the interior cavity of the segmented first shell 316 and to be attached thereto. The steps for attachment of the cup 406 to the first shell 316, by snap ring 445 are the same as discussed above for attaching the cup 106 to the second shell 70.

The next steps relate to the installation of the shaft 414. The shaft 414 is installed by the same steps used to install the shaft 114, as described above. FIG. 23 shows the completed installation of the prosthetic component 310.

The surgeon may determine that the prosthetic component 310 will not make a proper fit without a second shell, but that the second shell could be formed as a single piece as shown in FIGS. 15 and 27 and still pass through the hole 458 as shown in FIG. 27. Therefore, he would select the prosthetic component 610, as shown in FIG. 15. The steps for installation of the prosthetic component 610 through the step for installation of the enlarged segments, will be the same steps as the steps for installation of the prosthetic component 10 through the installation of the first shell 116. The steps for installing the single piece second shell 670 will require that the shell 670 be sized to pass through the hole 458. The shell 670 will then be inserted into the interior of the first shell 616 and attached thereto by a snap ring, in the same manner that the cup 106 was attached to the second shell 70, as discussed above. In a preferred embodiment of the prosthetic component 610, the solid (single piece) second shell 616, when made of synthetic resin, may be bonded to the first shell by pressure and temperature.

The next steps relate to the installation of the shaft 714. The shaft 714 is installed by the same steps used to install the shaft 114, as described above. FIG. 27 shows the completed installation of the prosthetic component 610, with the ball 710 inserted into the cup 706.

The surgeon may determine that none of the segmented acetabulums will be appropriate and may insert any of the well known acetabulums directly into the prepared hip socket. These acetabulums must be selected that have a cup sized to receive the ball 110 and ball 710.

The steps for implantation include the use of an expandable drill bit 166 for removal of the head of the femur and a portion of the acetabulum prior to placement of the prosthetic components. FIGS. 28–33 disclose a preferred embodiment of an expandable drill bit 166. In FIG. 28, the expandable drill bit is shown extending through the sleeve 160. The expandable drill bit 166 comprises a plurality of blades 168, a body 190 and a central hollow shaft 192 that includes a plurality of supports 194. As seen in FIG. 29, the top plan view of the apparatus of FIG. 32, a support 194 is attached to the first end 196 of the shaft 192, and at least one additional support 194, as seen in FIG. 28, is spaced along the length of the shaft 192. The support 194 has a hole 193 therethrough for receiving the guide wire 152 therethrough and a plurality of holes 195 that permits water to pass therethrough for flushing the site. The second end 198 of the shaft 192 is insertable in a drill motor 200, as shown in FIG. 34, for rotation of the shaft 192 and the blades 168 of the expandable drill bit 166.

Figure 32:
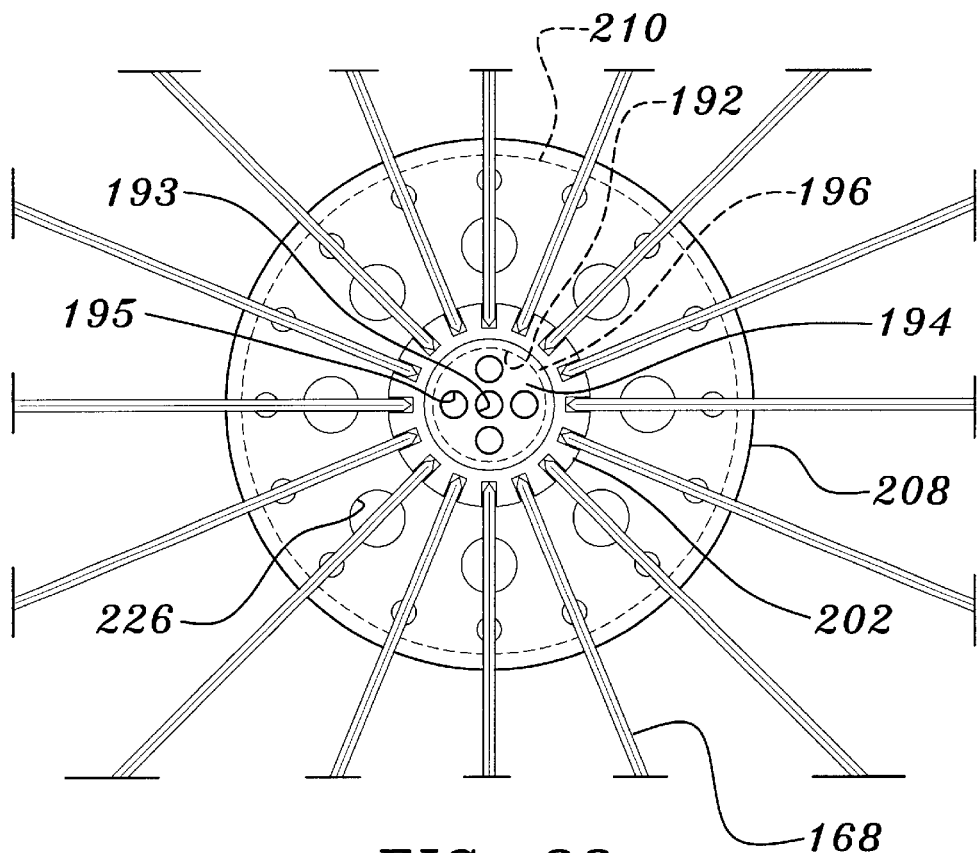
FIG. 32 is a detailed top plan view of FIG. 28.
Figure 33:
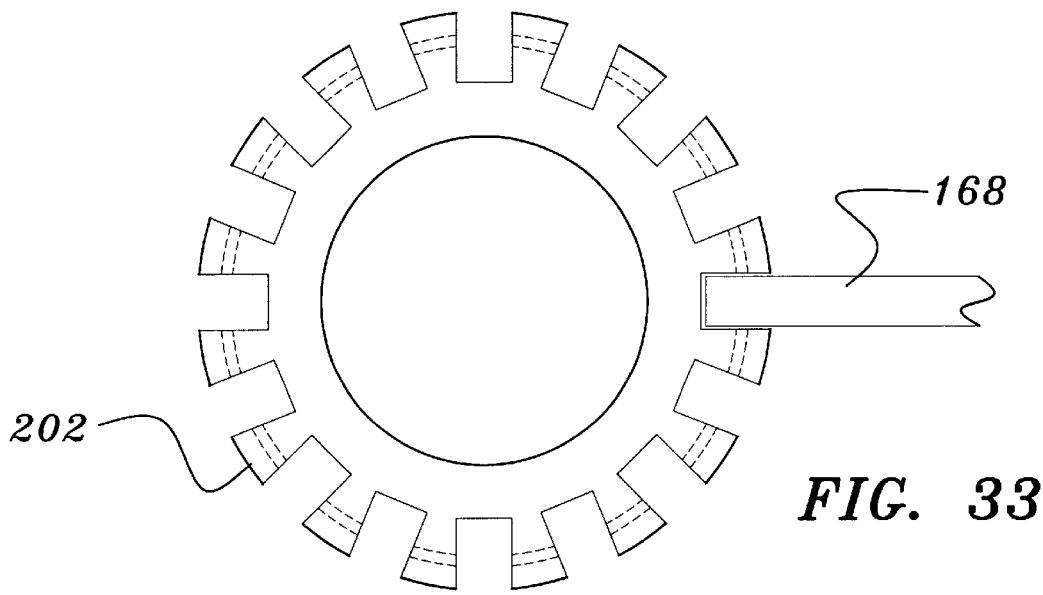
FIG. 33 is a detailed view of the means for attachment of the blades to the expandable drill bit of FIG. 28.

Annular plate 202, as shown in FIGS. 32 and 33, is attached to the first end 196 of the shaft 192 for attachment of the blades 168 to the shaft 192. Each blade 168 has one end of a stiff wire 204 attached to a hole 206 in a respective blade of the plurality of blades 168. The other end of the stiff wire 204 is attached to the end support plate 208 which is mounted to the first end 210 of the body 190. The body 190 is slideably mounted on the shaft 192 for expansion and retraction of the blades 168. A flexible wire 212 is passed through the holes 214 of the blades 168 as a safety measure to prevent the blades from expanding beyond a predetermined arc with a radius matching the finished radius of the acetabulum.

The hollow shaft 192 provides a means for delivering a flushing fluid to the cutting site through the port 216, which is connected to a pressurized water supply, (not shown). The port 216 is connected to a fixed annular ring 218, as seen in detail FIG. 29, that is sealingly attached to an annular cavity 217 that extends about the body 190 so that the body 190 may rotate inside the ring and maintain the port 216 in fluid flow communication with annular cavity 217 and the hollow shaft 192. A water source is attached to the port 216 by any well known means. Suction may be applied to port 220 by any well known suction device (not shown). Port 220 is connected in fluid flow communication with the interior of the body 190 through a fixed annular ring 224, for rotation of the body 190 therein, and an annular cavity 222. This permits suctioning the flush water and debris from the hip joint site through the plurality of holds 226 through the end plate 208 and the hollow body 190.

As the body 190 is free to slide longitudinally on the shaft 192, it is also free to rotate about the longitudinal axis of the shaft 192. During a cutting operation the body 190 must rotate with the shaft 192 to maintain the wires 204 in proper orientation. Therefore, thumbscrew 228 is tightened to rotate the body 190 with the shaft 192 and is loosened when adjustments are made to the angle of the blades 168. For adjustments to be made to the blades 168, the drilling must be stopped, the thumb screw 228 loosened, and the body moved along the shaft 192.

As discussed previously, each blade 168 has an outer cutting edge 170 and an inner cutting edge 172. The outer cutting edge is used primarily for cutting through the head of the femur and cutting the acetabulum to its predetermined curvature. The inner cutting edge is used to further trim the neck and head of the femur to ensure adequate clearance for free movement of the prosthetic joint.

While the foregoing describes particularly preferred embodiments of the present invention, it is to be understood that numerous variations and modifications of the structure of the prosthetic components and the method for implantation will occur to those skilled in the art. Accordingly, the foregoing description is to be considered illustrative only of the principles of this invention and is not to be considered limitative thereof, the scope of the invention being determined solely by the claims appended hereto.

What is claimed is:

1. A method for installing a joint prosthesis, comprising the steps of:

preparing a patient for surgery, the patient having a femur, the femur having a neck and a head, the patient further having a hip bone, said hip bone having a surface and an acetabulum formed thereon, and the acetabulum having a geometric center;

aligning the patient's body so that a longitudinal axis extending through the neck and head of the femur of the patient passes generally through the geometric center of the acetabulum of the patient, the longitudinal axis extending outwardly from the head and through the neck of the femur defining a point on the femur at which the longitudinal axis exits the femur;

making an incision to expose the femur generally at the point at which the longitudinal axis exits the femur;

boring a hole through the femur;

inserting an expandable drill bit into the hole in the femur and removing at least a major portion of the head of said femur, said drill bit having blades that are expandable;

inserting said expandable drill bit beyond said hole in said femur, expanding said blades of said expandable drill bit, and advancing said expandable drill bit until said blades of said expandable drill bit remove a portion of the acetabulum of said patient;

contracting the blades of said expandable drill bit and removing said expandable drill bit from the hole in the femur;

inserting a segmented first shell through the hole in the femur;

attaching said segmented first shell to the hip bone of the patient;

inserting a cup through the hole in said femur and mounting said cup in said segmented first shell;

inserting a shaft into the hole through the femur, said shaft having a first end and a ball on said first end of said shaft, said ball being sized and configured to be received by said cup, said shaft being inserted into the hole in the femur until said ball is received by said cup for movement therein; and closing said incision.

2. A method for installing a joint prosthesis as in claim 1, comprising the further steps of, inserting a guide wire through said femur, coincident with said longitudinal axis, and into the geometric center of the acetabulum of the patient;

using said guide wire to align a drill used to bore the hole through the femur, and using said guide wire to align said expandable drill bit while removing the head of said femur and drilling the hip bone.

3. A method for installing a joint prosthesis as in claim 1, comprising the further steps of, inserting a sleeve, having a first end, into the hole after boring the hole through said femur, such that said first end of said sleeve lies proximal said head of said femur.

4. A method for installing a joint prosthesis as in claim 1, comprising the further steps of, after removing a portion of the acetabulum, withdrawing said expandable drill bit keeping said blades expanded, each said blade having an interior cutting edge, the withdrawal of said expandable drill bit causing said interior cutting edge on said blades to engage and cut at least an additional portion of the head of the femur, whereby clearance between said femur and said acetabulum is increased.

5. A method for installing a joint prosthesis as in claim 1, wherein said segmented first shell comprises a base and a plurality of segments, the installation comprising the further steps of, inserting the base through the hole in said femur and attaching said base to said acetabulum; and successively inserting segments of said plurality of segments through the hole in the femur and mounting said segments to said base so that said segments engage one another and form a segmented first shell.

6. A method for installing a joint prosthesis as in claim 5, wherein said base has a plurality of secondary guide wires extending outwardly therefrom, comprising the further steps of, when inserting said segments through the hole in the femur, mounting each segment on a respective secondary guide wire and sliding each said segment on said secondary guide wire until each segment engages said base.

7. A method for installing a joint prosthesis as in claim 1, further comprising the steps of inserting a second shell through the hole in said femur, inserting said second shell into the interior of said segmented first shell and inserting said cup into the interior of said second shell.

8. A method for installing a joint prosthesis as in claim 7, wherein said second shell comprises a plurality of part,s each of said plurality of parts having a first end, further comprising the steps of; attaching the first ends of said plurality of parts to one another, inserting said plurality of parts through the hole in the femur and spreading said parts such that each side of each part, of said plurality of parts, lies adjacent to the side of at least one other part, of said plurality of parts, to form said second shell, and attaching said second shell to said segmented first shell.

\* \* \* \* \*